(12) United States Patent
Crawford et al.

(10) Patent No.: US 7,273,753 B2
(45) Date of Patent: *Sep. 25, 2007

(54) PURIFICATION AND USES OF DENDRITIC CELLS AND MONOCYTES

(75) Inventors: Keith D. Crawford, Newton, MA (US); Chester A. Alper, Brookline, MA (US)

(73) Assignee: Center of Blood Research, Boston, MA (US)

( * ) Notice: Subject to any disclaimer, the term of this patent is extended or adjusted under 35 U.S.C. 154(b) by 604 days.

This patent is subject to a terminal disclaimer.

(21) Appl. No.: 10/353,494

(22) Filed: Jan. 29, 2003

(65) Prior Publication Data

US 2004/0038398 A1    Feb. 26, 2004

Related U.S. Application Data

(63) Continuation-in-part of application No. 09/774,948, filed on Jan. 31, 2001, now Pat. No. 6,589,526, which is a continuation of application No. 08/902,246, filed on Jul. 29, 1997, now Pat. No. 6,194,204.

(60) Provisional application No. 60/023,028, filed on Aug. 2, 1996.

(51) Int. Cl.
C12N 5/00 (2006.01)
C12N 5/06 (2006.01)
C12N 5/08 (2006.01)

(52) U.S. Cl. .................. 435/325; 435/355; 435/372

(58) Field of Classification Search .............. None
See application file for complete search history.

(56) References Cited

U.S. PATENT DOCUMENTS

| | | | |
|---|---|---|---|
| 5,395,688 A | 3/1995 | Wang et al. | |
| 5,643,786 A | 7/1997 | Cohen et al. | |
| 5,648,219 A | 7/1997 | MacKay et al. | |
| 5,849,589 A * | 12/1998 | Tedder et al. | 435/377 |
| 6,194,204 B1 * | 2/2001 | Crawford et al. | 435/372 |
| 6,589,526 B2 * | 7/2003 | Crawford et al. | 424/93.71 |

FOREIGN PATENT DOCUMENTS

WO        WO95/34638        12/1995

OTHER PUBLICATIONS

Caux et al., J. Exp. Med. 184: 695-706 (Aug. 1996).*
Sporn et al. 2000. Chemoprevention of cancer. Carcinogenesis 21: 525-530.*
Whitacre et al. 1996. Treatment of autoimmune disease by oral tolerance to autoantigens. Clinical Immunology and Immunopathology 80: S31-39.*
Brod et al. 1996. Multiple sclerosis: clinical presentation, diagnosis and treatment. American Family Physician 54: 1301-1306 and 1309-1311.*
Fox. 1996. Clinical features, pathogenesis, and treatment of Sjogren's syndrome. Current Opinion in Rheumatology 8: 438-445.*
Myers et al. 1985. Redistribution of protein kinase C activity in human monocytes: correlation with activation of the respiratory burst. Journal of Immunology 135: 3411-3416.*
Crawford et al. 1999. Circulating CD2+ monocytes are dendritic cells. Journal of Immunology 163: 5920-5928.*
Richardson, The End of the Self, Discover, pp. 80-87 (Apr. 1996).
Hsu et al., Vaccination of patients with B-cell lymphoma using autologous antigen-pulsed dendritic cells, Nature 2:52-59 (1996).
Karhumaki et al., An improved enrichment method for functionally competent, highly purified peripheral blood dendritic cells and its application to HIV-infected blood samples, Clin. Exp. Immunol. 91:482-488 (1993).
Thomas et al., Isolation and Characterization of Human Peripheral Blood Dendritic Cells, J. of Immunology 150:821-834 (1993).
Inaba et al., Generation of Large Numbers of Dendritic Cells from Mouse Bone Marrow Cultures Suppl—mented with Granulocyte/Macrophage Colony-stimulating Factor, J. Exp. Med. 176:1693-1702(1992).
Miltenyi et al., High Gradient Magnetic Cell Separation with MACS, Cytometry 11:231-238 (1990).
Arulanandam and Reinherz, T11.1 Epitope mapping of Workshop anti-CD2 mAb using human CD2 adhesion domain mutants derived by site-directed mutagenesis, Leucocyte Typing V, Antigens, White Cell Differentiation, Schlossman et al., editor, Oxford University Press. vol. 1, pp. 344-345 (1995).
Zhou et al., A Novel Cell-Surface Molecule Expressed by Human Interdigitating Reticulum Cells, Langerhans Cells and Activated Lymphocytes is a New Member of the Ig Superfamily. J. Immunol. 149:735-742 (1992).
Triglia et al., Rapid Changes in Surface Antigen Expression by Blood Monocytes Cultured in Suspension or Adherent to Plastic, Blood 65:921-928 (1985).
Denning. S., T11 CD2 cluster report, Leucocyte Typing V, White Cell Differentiation Antigens, Schlossman et al., editor, Oxford University Press, vol. 1, pp. 342-343 (1995).
Siliciano et al., Activation of cytolytic T lymphocyte and natural killer cell function through the T11 sheep erythrocyte binding protein, Nature 317:428-430 (1985).
O'Doherty et al., Dendritic Cells Freshly Isolated from Human Blood Express CD4 and Mature into Typical Immunostimulatory Dendritic Cells after Culture in Monocyte-conditioned Medium, J. Exp. Med. 178:1067-1078 (1993).
Zhou and Tedder, Human Blood Dendritic Cells Selectively Express CD83, A Member of the Immunoglobulin Superfamily, J. of Immunol. 154:3821-3835 (1995).
Crawford et al., A novel lymphocyte restricted antigen which is exclusively expressed by human circulating dendritic leukocytes, Blood 80(10) Suppl. 1:192a (1992).

(Continued)

Primary Examiner—Irene Marx
Assistant Examiner—Lora E Barnhart
(74) Attorney, Agent, or Firm—Gosz & Partners LLP

(57) ABSTRACT

Methods for the preparation of substantially purified populations of dendritic cells and monocytes from the peripheral blood of a mammal is described. Also described are vaccine compositions and methods for the treatment of certain diseases and medical conditions based on the substantially purified dendritic cells and monocytes.

7 Claims, 11 Drawing Sheets

OTHER PUBLICATIONS

Bowden et al., T11.2 Epitopes and functional responses defined by Workshop anti-CD2 mAb, Leucocyte Typing V, Antigens, White Cell Differentiation, Schlossman ed. Oxford University Pr ss, vol. 1, pp. 346-347 (1995).

Reinherz et al., The Biology of Human CD2, Cold Spring Harbor Symposia on Quantitative Biology, vol. LIV 611-625 (1989).

Barclay et al., The Leucocyte Antigen Facts Book, Academic Press, pp. 104-113, 116-119, 124-127, 136-137, 142-145, 154-155, 228-229 (1993).

Arulanandam et al., The CD58 (LFA-3) binding site is a localized and highly charged surface area n the AGECC'C" face of the Human CD2 adhesion domain. PNAS USA 90:11613-11617 (1993).

Caux et al., Recent advances in the study of dendritic cells and follicular dendritic cells, Immunology Today, 16(1):2-4 (1994).

Becton Dickinson Immunocytometry Systems, 2350 Qume Drive, San Jose, CA 95131-1807, Monoclonal Antibodies Detecting Human Antigens, CD5 (Leu™-1), Source Book Section 4.1.1-4.1.3, 1993.

Becton Dickinson Immunocytometry Systems, 2350 Qume Drive, San Jose, CA 95131-1807, M noclonal Antibodies Detecting Human Antigens, CD14 (Leu™-M3), Source Book Section 4.25.1-4.25.2, 1993.

Miltenyi Biotec GmbH, Friedrich-Ebert-Strasse 68, 51429 Bergisch Gladbach, Germany—Press Release—New MACS Blood Dendritic Cell Isolation Kit, Cologne, Germany, Aug. 31, 1995.

* cited by examiner

A

B

```
                      SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: forward primer

<400> SEQUENCE: 1
acggcgttac tgatggtgct gctc                                              24

<210> SEQ ID NO 2
<211> LENGTH: 24
<212> TYPE: DNA
<213> ORGANISM: Artificial Sequence
<220> FEATURE:
<223> OTHER INFORMATION: reverse primer

<400> SEQUENCE: 2
tgaatgctgc ctgggtagaa atcc                                              24

<210> SEQ ID NO 3
<211> LENGTH: 21
<212> TYPE: DNA
<213> ORGANISM: Artificial Sequence
<220> FEATURE:
<223> OTHER INFORMATION: forward primer

<400> SEQUENCE: 3
agatgacctg caaaaccaca c                                                 21

<210> SEQ ID NO 4
<211> LENGTH: 19
<212> TYPE: DNA
<213> ORGANISM: Artificial Sequence
<220> FEATURE:
<223> OTHER INFORMATION: reverse primer

<400> SEQUENCE: 4
ggcccaaatc cttccacag                                                    19
```

```
<210> SEQ ID NO 5
<211> LENGTH: 20
<212> TYPE: DNA
<213> ORGANISM: Artificial Sequence
<220> FEATURE:
<223> OTHER INFORMATION: forward primer

<400> SEQUENCE: 5
cgtggacatc cgtaaagacc                                           20

<210> SEQ ID NO 6
<211> LENGTH: 21
<212> TYPE: DNA
<213> ORGANISM: Artificial Sequence
<220> FEATURE:
<223> OTHER INFORMATION: reverse primer

<400> SEQUENCE: 6
acattctgct ggaaggtgga c                                         21
```

PURIFICATION AND USES OF DENDRITIC CELLS AND MONOCYTES

CROSS REFERENCE TO RELATED APPLICATIONS

This application is continuation-in-part of U.S. application Ser. No. 09/774,948 filed on Jan. 31, 2001 now U.S. Pat. No. 6,589,526, which is a continuation of U.S. application Ser. No. 08/902,246 (now U.S. Pat. No. 6,194,204), filed on Jul. 29, 1997, which claims the benefit of U.S. Provisional Application No. 60/023,028, filed Aug. 2, 1996, each of which are incorporated herein by reference thereto in their entirety.

GOVERNMENT SPONSORED RESEARCH OR DEVELOPMENT

The U.S. Government may have a paid-up license in this invention and the right in limited circumstances to require the patent owner to license others on reasonable terms as provided for by the terms of Grant No. 5 P01 HL29583 awarded by the National Institutes of Health, and Grant No. DAMD17 awarded by the U.S. Department of Defense.

BACKGROUND OF THE INVENTION

This invention relates to substantially pure, isolated populations of monocytes and dendritic cells, methods of obtaining such purified cell populations, the use of such purified cells for immune and cancer therapy, transplant rejection and T-cell suppression or anergy (immunotolerance), the preparation of vaccines against immune diseases and cancer, the activation of dendritic cells by, for instance, ligation with a CD58 fusion protein, and for stimulating the production of IL-12 in vivo without the systemic use of a cytokine.

Dendritic cells are antigen-presenting cells found in all tissues and organs, including the blood. Specifically, dendritic cells present antigens for T lymphocytes, i.e., they process and present antigens, and stimulate responses from naive and memory T cells. In addition to their role in antigen presentation, dendritic cells directly communicate with non-lymph tissue and survey non-lymph tissue for an injury signal (e.g., ischemia, infection, or inflammation) or tumor growth. Once signaled, dendritic cells initiate the immune response by releasing IL-1, TNFα, and various other inflammatory cytokines which trigger lymphocytes and myeloid cells. Various immunodeficiencies, e.g., towards tumors, are thought to result from the loss of dendritic cell function.

Monocytes may also be involved in T-cell suppression and autoimmune diseases. These cells may play a role in blocking transplant rejection by suppressing T-cell and B-cell activation, thus preventing T-cell or antibody cytopathetic effects.

Accordingly, it would be desirable to obtain substantially pure populations of non-cytokine treated monocytes and dendritic cells in order to exploit the role of these cells in immunotherapy, cancer therapy and T-cell suppression. The isolation of these cells is difficult, however, due to the low frequency of occurrence of the cells in the circulating white cell population of the mammal, and because of the lack of a surface marker expressed by fresh and cultured dendritic cells to distinguish them from monocytes.

Conventional methods for cell isolation which enrich subpopulations of cell mixtures include, e.g. density gradient separation, fluorescence activated cell sorting, immunological cell separation techniques such as panning, complement lysis, resetting, magnetic cell separation techniques, and nylon wool separation. Different patterns of expression of cell surface antigens have been used in some cases to identify different cell types. Certain disadvantages of many of these reported methods are that they can be time-consuming, labor-intensive, costly, require large amounts of reagent, result in low specificity, low sensitivity, contaminated mixtures, poor and/or inaccurate separation, and the loss of desired cells. Certain other methods, such as the treatment of the cell population with cytokines, can change the properties, functions, or viability of the desired cells. Thus, prior methods generally are inefficient, time-consuming, expensive, and do not optimize for pure populations.

Commonly assigned U.S. Pat. No. 6,194,204 discloses that although both dendritic cells and monocytes express roughly the same levels of CD14, CD-2 is an effective marker for dendritic cells and can be used to separate dendritic cells and monocytes in mixed cell populations. This patent also discloses that a vaccine for treating cancer can be prepared from dendritic cells which express CD 14, preferably treated with or induced to express cancer-specific antigen to stimulate host cell immunity to the cancer upon administration.

Accordingly, it is an objective of this invention to provided substantially pure, isolated populations of dendritic cells and monocytes, and methods for preparing such substantially pure populations.

It is another objective of this invention to provide vaccines for use against a wide variety of diseases, such as cancer or AIDS, and to provide therapeutic formulations for the suppression of T-cell activity for the treatment of autoimmune disease or in the treatment of organ transplant rejection.

It is a further objective to treat a mammal having cancer or an immune disease, or to treat a mammal to prevent organ or tissue rejection.

It is a still further objective of this invention to provide a method for stimulating IL-12 activity in vivo in a mammal at targeted tissues and organs.

It is an additional objective of this invention to provide therapies for the treatment of autoimmune diseases.

SUMMARY OF THE INVENTION

According to the invention, a method for preparing substantially pure populations of dendritic cells or moncytes is provided. The method of this invention involves treating a biological fluid containing a mixed population of dendritic cells and monocyte cells, such blood or tissue, i.e. as the peripheral blood of a mammal, and separating the dendritic cells from the remaining cell population. The biological fluid can contain components other than dendritic and monocyte cells typically found in mammalian peripheral blood, such as disclosed in U.S. Pat. No. No. 6,194,204, the pertinent disclosure of which is incorporated herein by reference thereto. These other cell components include, without limitation, lymphocytes, T cells, NK cells, and B cells.

There are several methods which allow the enrichment of myeloid cells from blood. Starting with the peripheral blood or tissue of a mammal, the mononuclear cells can be separated from the peripheral blood into a first cell population having substantially lymphocytes, e.g., T cells, NK cells, B cells or mixtures thereof, and a second cell population having an enriched population of substantially myeloid cells. These myeloid cells can then be separated into a third cell population having substantially pure monocytes and a fourth cell population of substantially pure dendritic cells.

In certain embodiments, the separation of the mononuclear cells into a first cell population having substantially lymphocyte cells and a second cell population having substantially myeloid cells comprises contacting the mononuclear cells with antibodies against the lymphocytes so as to form an antibody-lymphocyte complex, and selectively separating the antibody-lymphocyte complex from the myeloid cells. The antibodies used can be, e.g., monoclonal antibodies, directed against one or more antigens which are expressed by one or more of the lymphocytes. For example, T cell antibodies include anti-CD3 antibodies, anti-CD8 antibodies, and mixtures thereof; NK cell antibodies include, e.g., anti-CD16/56 antibodies; and B cell antibodies include, e.g., anti-CD19 and anti-CD20 antibodies.

In certain embodiments, the antibody-lymphocyte complex that is formed is selectively separated from the myeloid cells by contacting the antibody-lymphocyte complex and the myeloid cells with a matrix such that the antibody-lymphocyte complex is substantially retained by the matrix, e.g., greater than 20%, 40%, 60%, 80%, 90%, 95%, 98%, or 99% retained, and the myeloid cells are substantially not retained by the matrix, e.g., greater than 20%, 40%, 60%, 80%, 90%, 95%, 98%, or 99% not retained.

Preferably, the antibody-lymphocyte complex further comprises magnetic beads, e.g., superparamagnetic microparticles. The magnetic beads can be attached, e.g., to the antibody, to the lymphocyte or to both. In embodiments in which the antibody-lymphocyte complex has magnetic beads, separation of such a complex from the myeloid cells preferably comprises contacting the myeloid cells and the complex with a magnetic matrix, e.g., magnetized steel wool, such that the antibody-lymphocyte complex having the magnetic beads is substantially retained by the magnetic matrix and the myeloid cells are substantially not retained by the magnetic matrix.

A variation of this method involves the use of fluorochromic agents attached to anti-CD2 antibodies to enable the flow cytometer to sort on the basis of size, granularity and fluorescent light. Thus, the flow cytometer can be configured to provide information about the relative size (forward scatter or "FSC"), graulatrity or internal complexity (side scatter or "SSC"), and relative fluorescent intensity of the cell sample. The fluorescent light sorts on the basis of CD2-expressing dendritic cells, enabling the cytometer to identify and enrich for dendritic cells and/or monocytes.

Another variation of this method involves separating the mononuclear cells into a first cell population having substantially lymphocytes and a second cell population having substantially myeloid cells by centrifugation.

In other embodiments, the dendritic cells can be directly selected from large populations of myeloid cells. This method can employ stem cell technology, or a solid phase method of enriching dendritic cells, using any agent that binds to CD2. The anti-CD2 complex can then be separated from the remaining cell components.

In certain embodiments, the separation of the myeloid cells into a third cell population having substantially monocytes and a fourth cell population having substantially dendritic cells comprises contacting the myeloid cells with antibodies against the dendritic cells so as to form an antibody-dendritic cell complex, and selectively separating the antibody-dendritic cell complex from the monocytes. The antibodies used, e.g., monoclonal antibodies, are directed against one or more antigens which are expressed by the dendritic cells, e.g, anti-CD2 antibodies. Suitable anti-CD2 antibodies include anti-T11$_1$, anti-T11$_2$, and anti-T11$_3$ antibodies.

The antibody-dendritic cell complex can further comprises magnetic beads. In this embodiment, separation of the antibody-dendritic complex from the monocytes preferably comprises contacting the monocytes and the antibody-dendritic cell complex having the magnetic beads with a magnetic matrix such that the antibody-dendritic cell complex having the magnetic beads is substantially retained by the magnetic matrix and the monocytes are substantially not retained by the magnetic matrix.

The retained antibody-dendritic cell complex can then be eluted from the matrix, e.g., by demagnetizing the matrix, e.g., by removing the matrix from the magnetic field.

Preferably, the dendritic cells in the fourth cell population are greater than about 60%, 70%, 80%, 90%, 95% 98%, or 99% pure. Preferably, the monocytes in the third cell population are greater than about 60%, 70%, 80%, 90%, 95%, 98%, or 99%% pure. Preferably, the monocytes in the third cell population and/or the dendritic cells in the fourth cell population are not activated as defined more particularly herein.

Another aspect of the invention is a method for the enrichment of dendritic cells from the peripheral blood of a mammal comprising selecting cells from the peripheral blood which express antigen CD2 and which also express antigen CD14.

The invention also includes a method for the enrichment of dendritic cells from the tissue of a mammal. Tissue having mononuclear cells from a mammal is provided. The mononuclear cells are separated from the tissue into a first cell population having substantially lymphocytes and a second cell population having substantially myeloid cells. The myeloid cells are separated into a third cell population having substantially monocytes and a fourth cell population having substantially dendritic cells.

Another aspect of the invention is a substantially purified population of mammalian dendritic cells that express antigen CD14 and antigen CD2. The dendritic cells can be activated by contact with an anti-CD2 antibody or CD58 fusion protein. By "substantially purified" is generally meant a population of cells greater than about 80% pure, more preferably greater than about 90% pure, and most preferably at least about 98% or 99% pure. The dendritic cells can be activated by contact with one or more anti-CD2 antibody. Such activated dendritic cells can be useful in the treatment of cancer, or any other disease that utilizes dendritic cells as an active component.

Accordingly, this invention also includes vaccines for treating mammals to prevent various disease states, such as cancers, inflammatory diseases and autoimmune diseases. Such a vaccine comprises a formulation including a therapeutically effective amount of substantially purified dendritic cells wherein said dendritic cells express antigen CD14 and antigen CD2. The formulation can also include various adjuvents and pharmaceutically acceptable carriers compatible with the dendritic cell formulation. The dendritic cells can be treated with disease-specific antigens, or fused with, for instance, cancer cells, for stimulating host immunity, for enhancing overall effectiveness, for targeting specific tissues or organs, and for predicting immune responsiveness. The dendritic cells are preferably activated by ligation with at least one anti-CD2 antibody in order to stimulate the production of IL-12 in vivo in the mammal.

A further aspect of this invention relates to a substantially purified population of monocytes that express antigen CD14 but not antigen CD2. This substantially pure population of monocytes can be obtained by separating the dendritic cells from a mixed population of dendritic cells and monocytes using the methods described above. The substantially pure monocytes can be formulated into therapeutic formulations for use in preventing organ transplant rejection, and for suppressing acitivated T cells. Suitable organ transplant procedures involve the kidney, liver, heart and lung.

This invention also includes a method for stimulating the production of IL-12 in vivo in a mammal comprising administering a population of substantially purified dendritic cells to the mammal. The substantially purified dendritic cells express CD14 and CD2 antigens, and said cells are preferably activated by ligation with at least one anti-CD2 antibody.

The various features and advantages of the present invention will be better understood from the following specification when read in conjunction with the accompanying drawings.

DETAILED DESCRIPTION OF THE INVENTION

Figure 1:
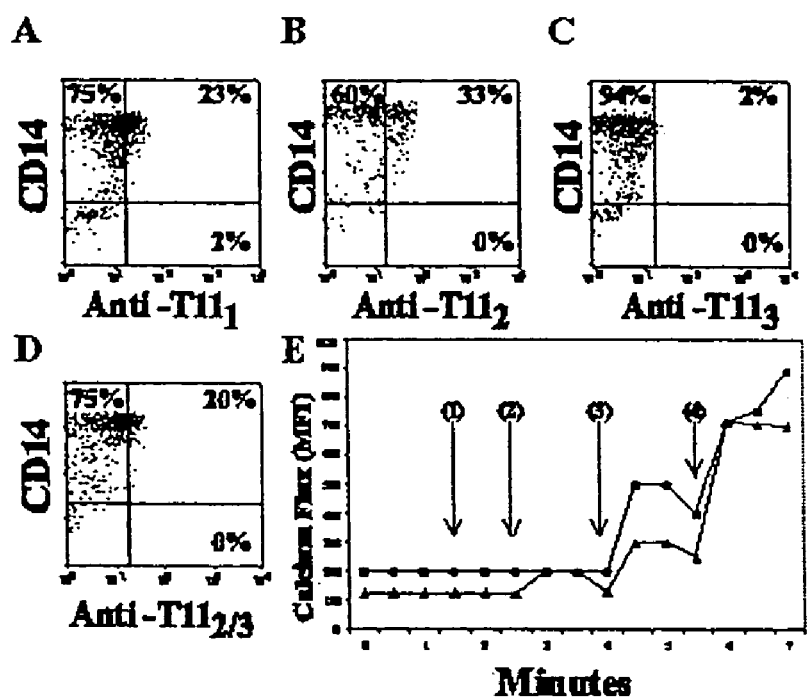
FIGS. 1A-E are graphs illustrating the phenotypic (1A-D) and functional mapping (1E) of the CD2 antigen on primary dendritic cells (pDC). $CD14^+$ monocytes were enriched from peripheral blood mononuclear cells by negative-selection and were shown to be negative for $CD3^+$ T cells or $CD56^+$ NK cells. Greater than 95% of the monocytes were $CD14^+$ (1A-D). Of the $CD14^+$ population, 30% and 37% stained positive with the anti-$T11_1$ (1A) or anti-$T11_2$ (1B) monoclonal antibodies, respectively. In contrast, anti-$T11_3$ antibody did not identify the CD2 antigen on the enriched monocytes (1C). However, when the $CD14^+$ population was incubated with the anti-$T11_2$ monclonal antibody for 30 minutes, and subsequently stained with anti-$T11_3$ monclonal antibody, 20% of the monocytes were $CD2^+$ (1D). $CD14^+$ myeloid (▲) and $CD3^+$ T cells (●) were incubated sequentially with anti-$T11_2$, anti-$T11_3$ and goat anti mouse monoclonal antibodies (1E), and changes in intracellular $Ca2^+$ were measured. Time (1) represents the addition of $T11_2$, (2) the addition of $T11_3$, (3) the addition of goat anti-mouse IgG, and (4) the addition of A23187 $Ca^{2+}$ ionophore. The results are representative of 3 experiments.

This invention provides substantially pure populations of monocytes and dendritic cells, and methods for preparing such substantially pure cell populations. Also provided are treatment methods employing such purified cell populations to treat disease states and medical conditions, such as for treating cancer, inflammatory diseases, transplant rejections and autoimmune diseases. This invention further provides for the stimulation of IL-12 production using such substantially purified cell populations.

By "peripheral blood", as used herein, is meant blood found in the circulation vasculature of a mammal. The peripheral blood can be obtained from any mammal.

A "mammal", as used herein, includes humans as well as non-human mammals. Preferred non-human mammals include primates, pigs, rodents, rabbits, canines, felines, sheep horses, and goats. Veterinary applications are within the scope of the present application.

Mammalian whole blood contains red blood cells and leukocytes. The red blood cells can be separated from the whole blood by any suitable method, such as lysis, positive selection or density segmentation. The remaining leukocytes population contains lymphocytes, myeloid cells and neutrophils. With the use of flow cytometry, or other suitable methods of comparing the relative size and granularity of the cells, these cell populations can be identified.

Mononuclear cells can be separated from the peripheral blood by any method known to those skilled in the art. Preferably, the method used does not affect cell function or viability. An example is the use of centrifugation, e.g., density gradient centrifugation, e.g., discontinuous density gradient centrifugation. Alternatively or in addition, monoclonal antibodies can be used. Starting material can also be mononuclear cells from peripheral blood or myeloid cells, rather than whole peripheral blood.

Mononuclear cells can be separated into a first cell population having substantially lymphocytes and a second cell population having substantially myeloid cells. The term "lymphocytes" includes, e.g. T cells, NK cells, B cells and mixtures thereof. By a cell population having "substantially lymphocytes" is meant that the cell population has greater than about 20% lymphocytes, preferably greater than 60%, and most preferably at least about 98%, or 99% lymphocytes. "Myeloid cells" are meant to include monocytes and dendritic cells. Monocytes are also meant to include macrophages. It is known that monocytes circulate in the peripheral blood, and when they migrate to the tissue, they are called macrophages. This lineage of cells is commonly known as the monocyte/macrophage lineage. Myeloid cells are generally CD14+, CD33+ and CD13+. By a cell population having "substantially mycloid cells" is meant that the cell population has greater than about 20% lymphocytes, preferably greater than 60%, and most preferably at least about 98%, or 99% lymphocytes.

The separation of the mononuclear cells into a first cell population having substantially lymphocytes and a second cell population having substantially myeloid cells can be performed by contacting the mononuclear cells with antibodies against the lymphocytes so as to form an antibody-lymphocyte complex, and selectively separating the antibody-lymphocyte complex from the myeloid cells. One or more than one type of antibody can be used for the separation of the mononuclear cells. The contacting and the selectively separating steps can be repeated, and can involve using the same type of antibody or antibodies against the lymphocytes, or a different type of antibody or antibodies against the lymphocytes.

Polyclonal and/or monoclonal antibodies can be used in this invention. Antibodies against the lymphocytes include, e.g., T cell antibodies, NK cell antibodies, B cell antibodies, or mixtures thereof. The antibodies used can be directed against one or more antigens which are expressed by one or more of the lymphocytes.

The T cell antibodies can be anti-CD3 antibodies. T cells express the CD3 surface molecule. CD3 is described in Barclay et al. ("The Leukocyte Antigen Facts Book", Academic Press Limited (1993), pp. 106-109). Anti-CD3 antibodies can be obtained from Becton Dickinson Immunocytometry Systems, San Jose, Calif., or Coulter Corp., Miami, Fla. Other T cell antibodies that can be used include, e.g. anti-CD8 antibodies. CD8 is also described in Barclay et al. (Id. at pages 118-119). Anti-CD8 antibodies can be obtained from Becton Dickinson Immunocytometry Systems or Coulter Corp. CD8 is expressed by about 40% of the T-lymphocyte population. Therefore, using, e.g. anti-CD8 antibodies may not result in the separation of the entire T cell population from the myeloid cells. There are, however, certain situations in which it might be desirable to use anti-CD8 antibodies. For example, CD8+ T lymphocytes represent a cytotoxic T-lymphocyte population. This population selectively targets and kills cells which are exposed to pathogen-specific antigens used in the production of pathogen-specific cytotoxic T cell lysis (intracellular pathogens).

The NK cell antibodies can be anti-CD16/56. CD16/56 refers to CD16 and CD56; they are not the same antigen, but are both expressed by NK cells (CD8+ T lymphocytes also express CD16). Anti-CD16/56 antibodies can be obtained from Becton Dickinson Immunocytometry Systems or Coulter Corp. The NK cell antibodies can be anti-CD8. Not all NK cells express CD8, and therefore using anti-CD8 antibodies may not result in the separation of the entire NK cell population from the myeloid cells.

The B cell antibodies can be anti-CD19 and/or anti-CD20 antibodies. CD19 and CD20 are expressed by resting and activated B lymphocytes. CD 19 and CD20 are described in Barclay et al. (Id. at pages 142-143 and 144-145, respectively). Anti-CD19 and anti-CD20 antibodies can be obtained from Becton Dickinson Immunocytometry Systems or Coulter Corp.

The antibody-lymphocyte complex that is formed can be selectively separated from the myeloid cells. This separation can include contacting the antibody-lymphocyte complex and the myeloid cells with a matrix such that the antibody-lymphocyte complex is substantially retained by the matrix, and the myeloid cells are substantially not retained by the matrix. Any matrix known in the art to be suitable for such separation can be used. A matrix that may be useful is a mesh of steel wool that is inserted into a plastic column and placed in a magnetic field. A cell magnetic bead complex passes into the matrix and remains in the matrix as long as the column stays within the magnetic field. Examples of matrices include depletion columns type BS, type CS, type D RS+, and MS+ used for Mini Mags separation. Such columns can be obtained from, e.g. Miltenyi Biotec, Auburn, Calif. The matrix can be provided in a column or in any way known to those skilled in the art, e.g. in a gel, on a filter, on a plate, on film or on paper. By the complex being substantially retained by the matrix is meant that greater than about 20% of the complex is retained, e.g. about 40% 60% 80% 95% or 98% is retained. By the myeloid cells being substantially not retained by the matrix is meant that greater than about 20% of the myeloid cells are not retained, e.g. about 40% 60% 80% 95% or 98% are not retained.

The antibody-lymphocyte complex can also include magnetic beads, e.g., superparamagnetic microparticles. Tetramer selection, non-magnetic particles, density gradient methods, and elutrication can also be used. A typical tetramer is the RosetteSep myeloid (CD33+) enrichment cocktail manufactured by StemCell Technologies, Inc. of Vancouver, British Columbia, Canada. Any type of magnetic beads known to those of skill in the art can also be used. Magnetic beads can be attached, e.g. to the antibody and/or to the lymphocyte. Such attached antibodies can be obtained, e.g. from Miltenyi Biotec, Auburn, Calif. (as MACS superparamagnetic microbeads conjugated with monoclonal antibodies), or from Dynal Corp., Lake Success, N.Y. (as detachable or non-detachable large magnetic beads). See also Miltenyi et al., *Cytometry* 11:231-238 (1990). Large magnetic beads (obtainable from Dynal Corp.), can be used for the removal of lymphocytes. Smaller beads (obtainable from Miltenyi Biotec), can be used for the enrichment of the dendritic cells. Magnetic beads can be attached prior to the formation of the antibody-lymphocyte complex, or subsequent to the formation of the complex.

Where the antibody-lymphocyte complex includes magnetic beads, separation of such a complex from the myeloid cells can include contacting the myeloid cells and the complex with a magnetic matrix such that the antibody-lymphocyte complex having the magnetic beads is substantially retained by the magnetic matrix and the myeloid cells are substantially not retained by the magnetic matrix. An example of a magnetic matrix is magnetized steel wool. Steel wool can be obtained from Miltenyi Biotec. The steel wool can be magnetized by, e.g. introducing it into a magnetic field, e.g. 0.6 Tesla, though other strength magnetic fields can also be used as known to those skilled in the art. The magnetic field can be produced, e.g. with a commercial electromagnet.

Antibodies to the T cells, NK cells and B cells can be contacted with the mononuclear cells prior to selectively separating the resulting antibody-lymphocyte complexes from the myeloid cells. Alternatively, antibodies to only one type of lymphocyte cell can be added (e.g. T cells), and the resulting antibody-lymphocyte complex can be separated from the remaining cells. Antibodies to one of the remaining types of lymphocytes (e.g. NK cells) can then be added to the remaining cells from the above procedure, and the resulting antibody-lymphocyte complex can be separated from these remaining cells. Finally, antibodies to the remaining type of lymphocyte (e.g. B cells) can then be added to this second batch of remaining cells, and the resulting antibody-lymphocyte complex can be separated from these remaining cells (predominantly the myeloid cells).

The separation of mononuclear cells into a first cell population having substantially lymphocytes and a second cell population having substantially myeloid cells, can also be carried out by centrifugation. The centrifugation can be, e.g., density gradient centrifugation. For example, metrizamide 14.5% (obtained from Sigma Chemical Co., St. Louis, Mo.) or Monocyte 1 step (which is a pre-made discontinuous gradient which separates lymphocytes from myeloid cells, obtained from Accurate Chemical and Scientific Corp., Westbury, N.Y.), can be used. Centrifugation procedures are most useful if there are initially a large number of PBMCs, e.g. about 109.

The separation of the mononuclear cells into a third cell population having substantially monocytes and a fourth cell population having substantially dendritic cells can be performed by contacting the myeloid cells with antibodies against the dendritic cells so as to form an antibody-dendritic cell complex, and selectively separating the antibody-dendritic cell complex from the monocytes. The selectively separating steps can be repeated, e.g. using the same type of antibody or antibodies, or a different type of antibody or antibodies against the dendritic cells.

Monoclonal antibodies can be used for the separation of monocytes and dendritic cells, as described in further detail below. The antibodies can be directed against one or more antigens that are expressed by the dendritic cells, e.g., anti-CD2 antibodies and/or anti-CD5 antibodies. Use of anti-CD2 antibodies is particularly beneficial because they stain greater than 95% of the dendritic cells and do not modulate down in culture. CD2 and CD5 are described in Barclay et al. (Id. at pages 104-105 and 112-113, respectively). Anti-CD2 antibodies can be obtained from Coulter Corp. Anti-CD5 antibodies can be obtained from Becton Dickinson Immunocytometry Systems or Coulter Corp.

Prior to contacting the myeloid cells with antibodies, the myeloid cells can be cultured, e.g. for about 12 hours to about 36 hours, in about 5% to about 10% pooled mammal specific serum. For example, pooled human serum can be used if the isolation is from human peripheral blood, and pooled pig serum can be used if the isolation is from pig peripheral blood. After such culturing, antibodies, e.g., anti-CD83 antibodies, can be used so as to form an antibody-dendritic cell complex. (CD83 is described in Zhou et al., *J. Immunol.* 154: 3821-3835 (1995); Crawford et al., *Blood* 80(10) Supplement 1:192a (1992)). Anti-CD83 antibodies can be isolated as described in Zhou et al., *J Immunol.* 149:735 (1992). The dendritic cells that are isolated in this embodiment can be phenotypically CD14.

An antibody-dendritic cell complex that is formed, e.g., as a result of using any of the antibodies described herein, can be selectively separated from the monocytes. The separation can include contacting the antibody-dendritic cell complex and the monocytes with a matrix such that the antibody-dendritic cell complex is substantially retained by the matrix and the monocytes are substantially not retained by the matrix. The retained antibody-dendritic cell complex can then be eluted from the matrix.

The antibody-dendritic cell complex can include magnetic beads, as described above. Where this is the case, separation of the antibody-dendritic complex from the monocytes can include contacting the monocytes and antibody-dendritic cell complex having the magnetic beads with a magnetic matrix such that the antibody-dendritic cell complex having the magnetic beads is substantially retained by the magnetic matrix and the monocytes are substantially not retained by the magnetic matrix. A retained antibody-dendritic cell complex can be eluted from the matrix, e.g., by demagnetizing the matrix, e.g., by removing the matrix from the magnetic field. This method allows the preparation of either a substantially purified subculture of monocytes, or a substantially purified subculture of dendritic cells.

The dendritic cells in the fourth cell population can be greater than about 60% pure, e.g., 70%, 80%, 90%, 95%, 98%, 99%, or greater than 99% pure. The dendritic cells in the fourth cell population can be substantially activated or unactivated. The dendritic cells can be activated by, e.g. culturing the dendritic cells with, for instance, an anti-CD2 antibody, such as anti-T11$_1$, anti-T11$_2$, and anti-T11$_3$ antibodies, or LFA-3 (CD58) ligand.

The monocytes in the third cell population can be greater than about 70% pure, e.g., 70%, 80%, 90%, 95%, 98%, 99%, or greater than 99% pure. The monocytes in the third cell population can be substantially activated or unactivated. An advantage of the present invention is that it can produce monocytes which are unactivated. Other monocyte isolation procedures which use plastic adherence are known to rapidly induce monocyte activation. See Triglia et al., *Blood* 65(4): 921-928 (1985). Substantially pure cultures of monocytes can produced by the methods of the present invention, and can be useful, e.g. for preventing transplant rejection in mammals.

Dendritic cells can be isolated from the peripheral blood of a mammal, for example, by selecting cells from the peripheral blood which do not express antigens CD3, CD16/56 and CD19 or CD20, and which do express antigen CD2.

Optionally, cells which also express, or do not express, antigen CD14 can be selected. It is preferred to select the dendritic cells on the basis of CD2 expression.

Dendritic cells can also be isolated from the tissue of a mammal. Tissue having mononuclear cells from a mammal is obtained, and the mononuclear cells are separated from the tissue. The mononuclear cells are separated into a first cell population having substantially lymphocytes and a second cell population having substantially myeloid cells. The myeloid cells are further separated into a third cell population having substantially monocytes and a fourth cell population having substantially dendritic cells. The tissue can be from any part of the body of the mammal that has dendritic cells, e.g., skin or lymph nodes.

Primary dendritic cells are found in most solid tissues of the body, and comprise less than 1% of the total cell content, while blood dendritic cells may represent up to 3-4% of the circulating peripheral blood mononuclear cells. The separation process described above can result in a substantially purified population of mammalian dendritic cells. Histogram analysis of the staining of leukocyte cell surface antigens has demonstrated that dendritic cells are CD14+. By "substantially purified population" is meant that greater than about 80% of the cells are dendritic cells, e.g., 85%, 90%, 95%, 99%, or greater than 99% are dendritic cells. The dendritic cells also express antigen CD2.

Substantially pure dendritic cells are useful for many clinical applications, e.g., in adoptive immunotherapy (such as for use in the production of pathogen specific CTL production or in antigen specific T helper cell production), or for vaccine-therapy (such as antigen pulsed dendritic cells reinjected into the patient), or for enhanced graft acceptance and monocyte suppression. The substantially pure dendritic cells are also useful in studies evaluating blood dendritic cell maturation and development; elucidation of CD2-LFA-3 signal transduction pathways; studies investigating primary immune response by antigen pulsed blood dendritic cells; analysis of tumor immunity by tumor-antigen exposed blood dendritic cells; studies evaluating HIV-1 infectivity by dendritic cells and pathogens; comparisons of antigen uptake processing and presentation of dendritic cells, particularly as compared to monocytes; and analysis of gene expression in blood dendritic cells.

The dendritic cell-based compositions of the present invention can also be used for treating diseases, e.g., cancer and autoimmune diseases. For example, the dendritic cells can be treated with a cancer specific antigen so as to stimulate host immunity to the cancer when the vaccine composition is administered to a mammal. The cancer can be any type of cancer, e.g., a solid tumor, e.g., B-cell lymphoma. "Mammal" is meant to include human as well as non-human mammals. "Treating" is meant to include, e.g., preventing, treating, reducing the symptoms of, or curing the cancer. The cancer-specific antigen can be any antigen that can be recognized by the immune system of the mammal, e.g., a cancer-specific idiotype protein. By "idiotype" is meant antigenic motifs formed by the combination of the variable regions of immunoglobulin heavy and light chains. Treatment of the dendritic cells with the cancer-specific antigen can be by any method which results in the dendritic cells presenting the antigen so as to stimulate host immunity when the vaccine composition is administered to the mammal, e.g., by pulsing or culturing the dendritic cells in the presence of the antigen prior to administration of the vaccine composition to the mammal.

The composition can include any pharmaceutically acceptable carrier known in the art. Further, the vaccine composition can include any adjuvant known in the art, e.g., Freund's complete or incomplete adjuvant.

By "therapeutically effective amount" is meant that amount which is capable of at least partially preventing or reversing the symptoms of the cancer. A therapeutically effective amount can be determined on an individual basis and will be based, at least in part, on a consideration of the species of mammal, the mammal's size, the dendritic cells used, the type of delivery system used and the time of administration relative to the progression of the cancer. A therapeutically effective amount can be determined by one of ordinary skill in the art employing such factors and using no more than routine experimentation.

Dendritic cells can be administered to the mammal by any method which allows the dendritic cells to reach the appropriate cells. These methods include, e.g., injection, infusion, deposition, implantation, oral ingestion, or topical administration, or any combination thereof. Injections can be, e.g., intravenous, intramuscular, intradermal, subcutaneous or intraperitoneal. Single or multiple doses can be administered over a given time period, depending upon the cancer, as can be determined by one skilled in the art without undue experimentation. The injections can be given at multiple locations. Administration of the dendritic cells can be alone or in combination with other therapeutic agents.

The present invention also features substantially pure cultures of hybrid dendritic cells and methods of making the same. The term "fused" or "fused dendritic cell" is used herein to refer to dendritic cells that have been fused with another type of cell, e.g., a cancer cell. Like the substantially pure cultures of dendritic cells described above, substantially pure cultures of fused dendritic cells have many applications, e.g., in adoptive immunotherapy (such as for use in pathogen specific CTL production or in antigen specific T helper cell production), or for vaccine-therapy (e.g., vaccines to treat cancer), or for enhanced graft acceptance. In treating cancer, for example, dendritic cells can be pulsed with tumor antigens and administered to a patient to treat, e.g., established tumors, or to prevent tumor formation, as discussed above. Hybridized dendritic cells can be particularly useful in situations where a tumor associated antigen exists but remains unidentified, making it impossible or inefficient to pulse or culture the dendritic cells with the antigen. A dendritic cell that has been fused with the target cancer cell can be administered to the patient, wherein the fused dendritic cell will, in its role as an antigen-presenting cell, present the antigen to the immune system. Dendritic cells can be fused with other cells, e.g., cancer cells, by any method known in the art. For example, methods for fusing dendritic cells and B cells with cancer cells, as well as methods for administering them to animals have been described in Gong et al. (Nat. Med. 3(5):558-561 (1997)) and Guo et al. (Science 263: 518-520 (1994)), both references being incorporated herein by reference in their entirety. Likewise, the cancer cell can be any type of cancer cell to be targeted in a patient, e.g., cancer cells of the breast, liver, skin, mouth, pancreas, prostate, urinary tract, e.g., bladder, uterus, ovary, brain, lymph nodes, respiratory tract, e.g., larynx, esophagus, and lung, gastrointestinal tract, e.g., stomach, large and small intestine, colon, or rectum, bone, blood, thyroid, and testes, or any cancer cell line known in the art to be suitable for fusing to other cells e.g., dendritic cells or B cells.

The CD2 antigen is a 50-55 kD molecular weight glycoprotein that was initially identified on T cells and NK cells and has been shown by the present inventors to be expressed by circulating dendritic cells. Antibodies to this surface antigen react strongly with resting T cells. CD2 is a member of the Ig superfamily, and is structurally similar to its principal ligand, LFA-3 (CD58). CD2 and LFA-3 interact through similar amino terminal ligand-binding regions. The interaction between CD2 on T cells and CD58 on antigen presenting cells is intimately involved in T cell-specific antigen recognition.

The CD2 surface antigen is divided into three regions reflecting their functional relationship. The first region, $T11_1$, is responsible for adhesion with the LFA-3 molecule and sheep erythrocyte binding. The first antibody that was produced to this region is anti-$T11_1$ and its clone designation is 3PTH29. The second region, $T11_2$, is an area on the CD2 antigen that does not interact with the binding domain but has been demonstrated to play a role in T cell activation in conjunction with a second antibody. The first antibody that was produced to this region is anti-$T11_2$, and its clone designation is IOLD24C1. Other anti-$T11_2$ clones include UMCD2/1E7E8,0275,9.6 and 7E10. The crosslinking of the $T11_2$ region with monoclonal antibodies induces unfolding of the CD2 antigen and exposure of a cryptic epitope. This cryptic epitope represents a third region, $T11_3$ or CD2R, and is expressed by activated T cells and cell lines, but only after exposure to $T11_2$ monoclonal antibodies (or others with similar traits), which induces a conformational change in structure of the CD2 antigen. The first antibody to this region is anti-$T11_3$, and its clone name is 1 mono2A6. Other $T11_3$ clones include VIT13, G144 and L304.

Dendritic cells can be activated via CD2 engagement with, e.g., anti-CD2 antibodies, e.g., $T11_1$, $T11_2$ or $T11_3$, or CD2 binding fragments thereof, or with LFA-3, or CD2 binding fragments thereof. The present invention contemplates the use of any one, any combination, or all, of these antibodies, antibody fragments, LFA-3 antigen, or LFA-3 fragments. Optionally, a cross linking antibody e.g., an antibody directed against any of the above antibodies, e.g., a goat anti-mouse IgG antibody, can be used to cross link any of the above antibodies following binding of the antibodies to an epitope on CD2. For example, a cross linking antibody can be used to cross link an anti-$T11_2$ antibody to an anti-$T11_3$ antibody, following binding of the anti-$T11_2$ and anti-$T11_3$ to CD2 on dendritic cells.

As used herein, the term "activate(d)" dendritic cell refers to the state induced in dendritic cells when the CD2 epitope on the dendritic cell is engaged. Activated dendritic cells may demonstrate any or all of the following: an increase in class II molecule expression; an increase in costimulatory molecule expression, e.g., increases in the expression of CD40, CD80, and CD86; an increase in adhesion molecule expression, e.g., CD54, CD58; release of cytokines, e.g., IL-12; and an increase in $Ca_{2+}$ mobilization.

The present invention contemplates methods for treating certain diseases in a mammal in need of such treatment using the substantially purified cells described herein. The dendritic cells or monocytes can be formulated into vaccine compositions comprising a therapeutically effective amount of the cells, a pharmaceutically acceptable carrier and other ingredients, such as adjuvants, Freund's complete or incomplete adjuvant, suitable for formulating such vaccine compositions as is known to those skilled in the art. Vaccines containing substantially purified dendritic cells can be used for the treatment of cancer and inflammatory conditions. Vaccines containing substantially pure monocytes can be used for preventing transplant rejection. The vaccine is administered to the mammal such that treatment of the disease occurs.

By "therapeutically effective" amount is meant that amount which is capable of at least partially preventing or reversing the symptoms of the disease. A therapeutically effective amount can be determined on an individual basis and will be based, at least in part, on consideration of the species of the mammal, the size of the mammal, the type of cells used, the type of delivery system used, and the type of administration relative to the progression of the disease. A therapeutically effective amount can be determined by one of ordinary skill in the art employing such factors and using no more than routine experimentation.

The vaccine can be administered to the mammal by any method which allows the dendritic cells or monocytes to reach the appropriate cells in the mammal. These methods include, without limitation, injection, infusion, deposition, implantation, oral ingestion or topical administration. Preferably, administration is by injection. Injections can be, e.g., intravenous, intramuscular, intradermal, subcutaneous or intraperitoneal. Single or multiple doses can be administered over a given time period, depending upon the disease, as can be determined by one skilled in the art without undue experimentation. In certain embodiments, the injections can be given at multiple locations. Administration of the vaccine can be alone or in combination with other therapeutic agents.

Also contemplated by the present invention is the modification of existing dendritic cell-based AIDS and tumor vaccines for increased effectiveness. Such vaccines can be phenotypically and functionally modified by activation or engagement of the CD2 present on the dendritic cells prior to vaccination of the patients. The CD2 activation of the dendritic cells increases the release of IL-12 without the need for additional cytokines, thereby improving the ability of the dendritic cell-based vaccines to promote antigen-specific T cell responsiveness and lessening the side effects associated with the systemic use of cytokines to help boost immunity.

Referring now to the accompanying drawings, the presence of CD2 on circulating primary dendritic cells has been observed. Thus, whether three distinct CD2 epitopes, $T11_1$, $T11_2$, and $T11_3$, are present on mature CDI4+ Mx was investigated with anti-$T11_1$ (FIG. 1A), anti-$T11_2$ (FIG. 1B), and anti-$T11_3$ (FIGS. 1C-D) mAbs. Anti-$T11_1$ and anti-$T11_2$ identified CD2 on 30% and 37% of the CD14+ Mx (FIGS. 1A-B) respectively, while none of the CD14+ Mx stained positive for CD2 with anti-$T11_3$. However, when CD14+ Mx were incubated for 30 min with anti-$T11_2$ and subsequently stained with anti-$T11_3$, 20% of the CD 14+ Mx were CD2+. Since these studies were performed at 4° C. and in medium that lacked $Mg^{++}$ and $Ca^{++}$ the conformational change in CD2 that exposes the $T11_3$ epitope was not temperature, $Ca^{++}$ or $Mg^{++}$ dependent.

Since CD2 ligation induces activation of T and NK cells, $[Ca^{++}]i$ mobilization was measured as an early intracellular activation event in CD14+ Mx and CD3+ T cells after CD2 ligation with anti-$T11_2$ and anti-$T11_3$ mAbs pairs (FIG. 1E). Samples were pulsed with anti-$T11_2$ [FIG. 1E (1)], and there was virtually no increase in $[Ca^{++}]i$. The subsequent addition of $T11_3$ [FIG. 1E (2)] induced a 69% increase in $[Ca^{++}]i$ in CD14+ Mx. Further addition of goat anti-mouse IgG [FIG. 1E(3)], which cross-linked the anti-$T11_2$ and anti-$T11_3$ mAbs previously bound to CD2, increased $[Ca^{++}]i$ in CD 14+ Mx by 95% above the baseline.

These results are compared to CD3+ T cells from the same donor (FIG. IE). No increase in $[Ca^{++}]i$ was seen upon addition of anti-$T11_2$ or anti-$T11_3$ mAbs [FIG. 1E (1 and 2)] to T cells. However, when goat anti-mouse IgG was added [FIG. 1E (3)], the level of $[Ca^{++}]i$ increased to 180% above baseline in the T cell sample. Furthermore, similar findings were demonstrated when Jurkat cells were assessed (data not shown). Collectively, these results strongly suggest that CD2 is a functional molecule on primary dendritic cells.

Figure 2:
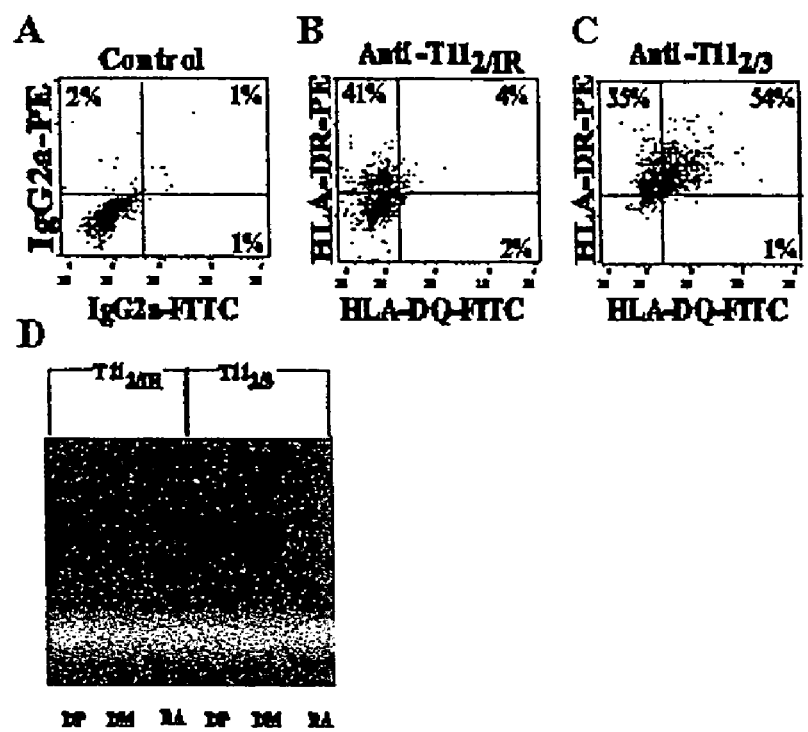
FIGS. 2A-D are graphs and plots that illustrate the induction of class II antigens of primary dendritic cells detected by immunofluorescence and molecular analysis after CD2 ligation. $CD14^+$ monocytes were precultured for 36 hours in 10% PHS, followed by anti-$T11_2$ enrichment of the primary dendritic cells. The enriched primary dendritic cells were resuspended in fresh 10% PHS at a final concentration of $10^6$ cells/ml for 12 additional hours in the presence an irrelevant antibody control (2A), or anti-$T11_3$ antibody (2B, 2C). Two-color analysis of each dendritic cell sample was performed with anti-HLA-DR and anti-HLA-DQ monoclonal antibodies. The quadrant boundaries were set using isotype controls (2A). RT-PCR (2D) was used to assess HLA-DP, HLA-DM, and β-actin gene expression of primary dendritic cells that were cultured in the presence of either anti-$T11_2$ and irrelevant antibody control or anti-$T11_2$ and anti-$T11_3$ monoclonal antibodies. The results are representative of 3 or more studies.

Because CD2 ligation induced increased $[Ca^{++}]i$, the effect of CD2 ligation on primary dendritic cell surface antigen expression was investigated. Immunofluorescence analysis of HLA-DR and HLA-DQ expression revealed that both molecules were upregulated with anti-CD2 mAb pairs (FIGS. 2A-C). HLA-DR levels increased 2-fold while HLA-DQ levels increased 9-fold. This upregulation of class II molecules on primary dendritic cells was dependent on the simultaneous binding of CD2 by anti-$T11_2$ and either anti-$T11_3$ (FIG. 2C) or anti-$T11_{11}$ mAbs (data not shown), and did not occur with $T11_2$ alone (FIG. 2B) or on monocytes (data not shown). To determine whether transcription of HLA-DP and -DM genes was altered by CD2 ligation, equal numbers of primary dendritic cells were incubated with anti-$T11_3$ (FIG. 2D). Following 24 hours of incubation, cDNA was generated and PCR was performed on equal amounts of cDNA for HLA-DM, HLA-DP, and β-actin. Primary dendritic cells cultured in the presence of anti-$T11_3$ mAb had higher levels of HLA-DM and HLA-DP mRNA than samples cultured in the presence of irrelevant antibody control and anti-$T11_2$ mAbs. Thus, as seen with HLA-DR and -DQ surface expression, anti$T11_3$ also induced HLA-DP and -DM gene activation in primary dendritic cells (FIG. 2D). These results provide further evidence that engagement of CD2 on primary dendritic cells increased class II molecule expression.

Figure 3A:
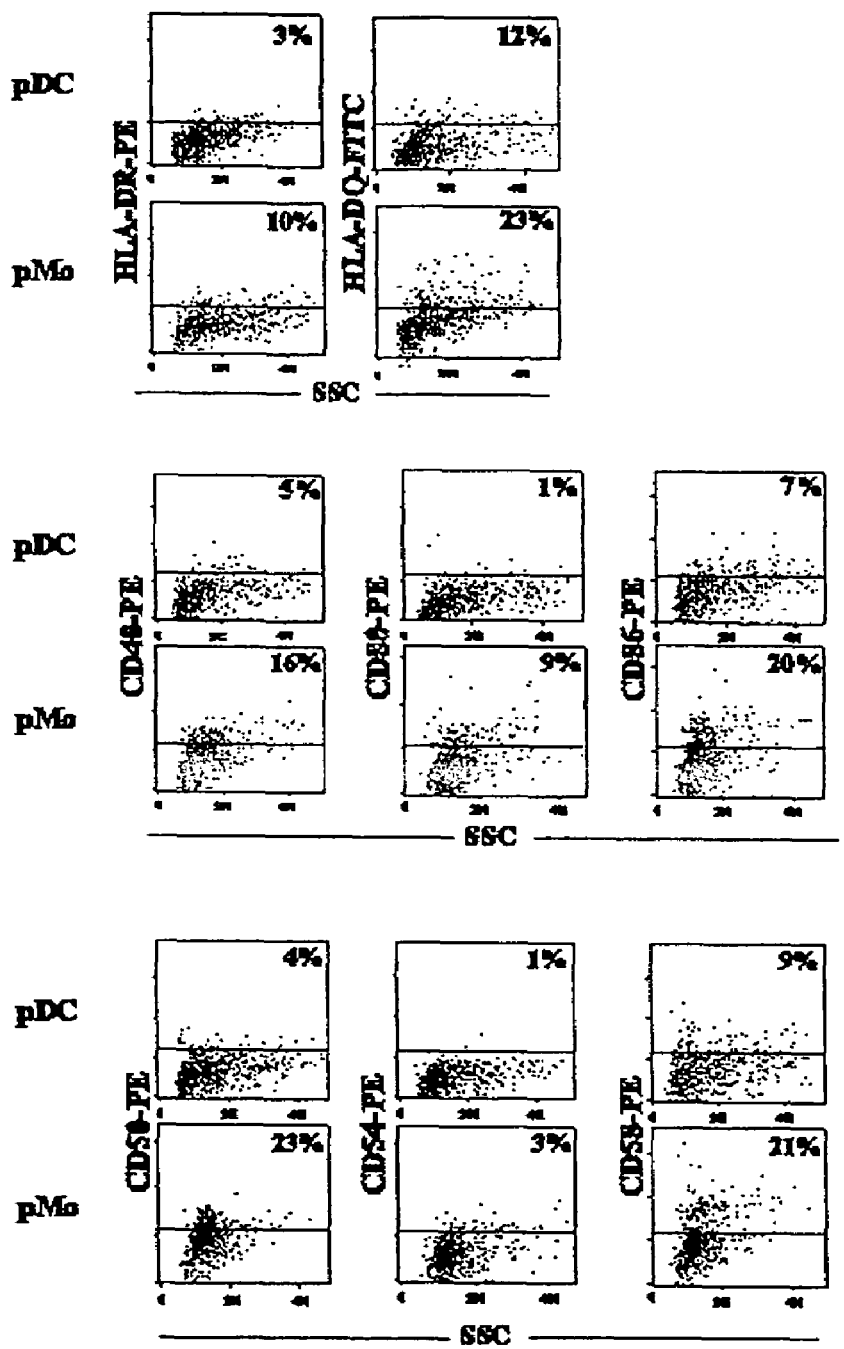
FIGS. 3A-C are graphs that illustrate the phenotypic characteristics of mature primary dendritic cells, primary monocytes, and monocyte-derived dendritic cells. $CD14^+$ monocytes were cultured in 10% PHS for 5 days, separated into mature primary dendritic cells and monocytes, and analyzed by flow cytometry (3A) for MHC class II costimulatory and adhesion molecules. Analysis of the same surface antigens on GM-CSF/IL-4-generated moncyte-derived dendritic cells (3B) was also performed. Primary dendritic cells and monocytes were recultured for 24 hours in fresh media, and the surface expression of the above molecules was reassessed (3C). Dot plots were divided into upper and lower regions, which represent high and low MFI populations. Results are representative of data from more than 3 experiments.
Figure 3B:
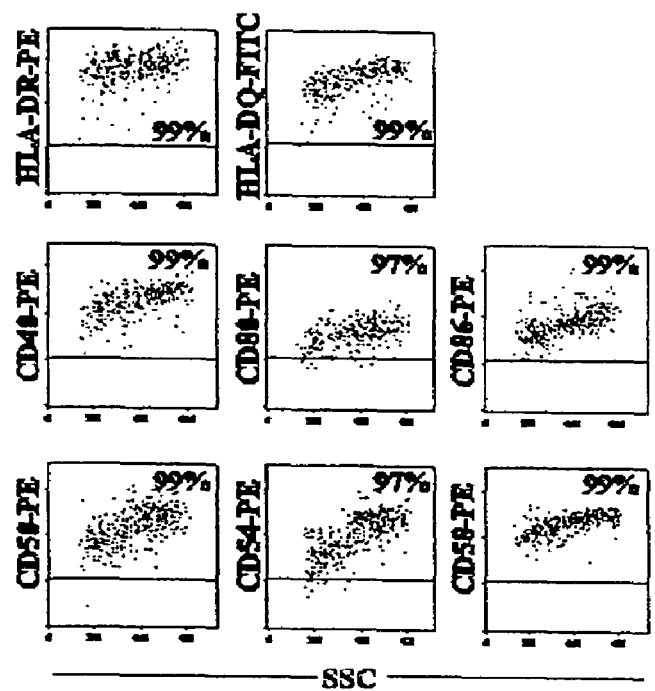
Figure 3C:
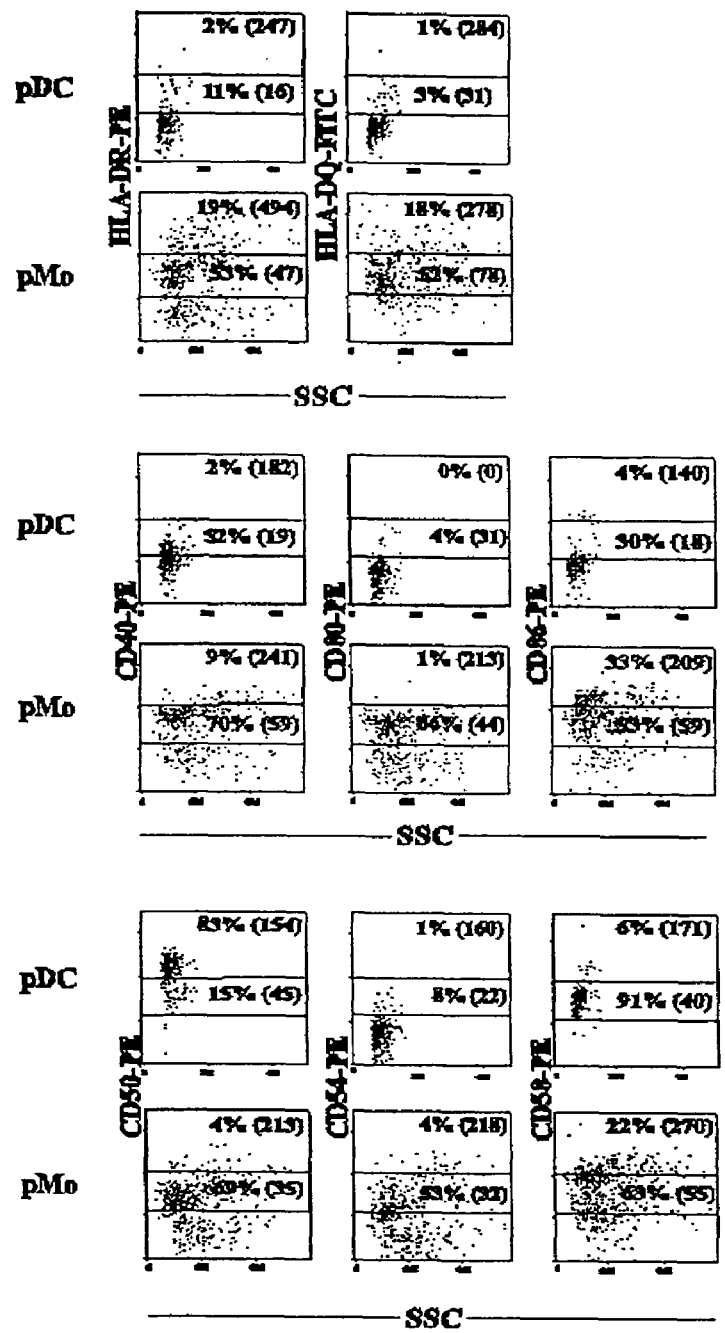
Figure 4A:
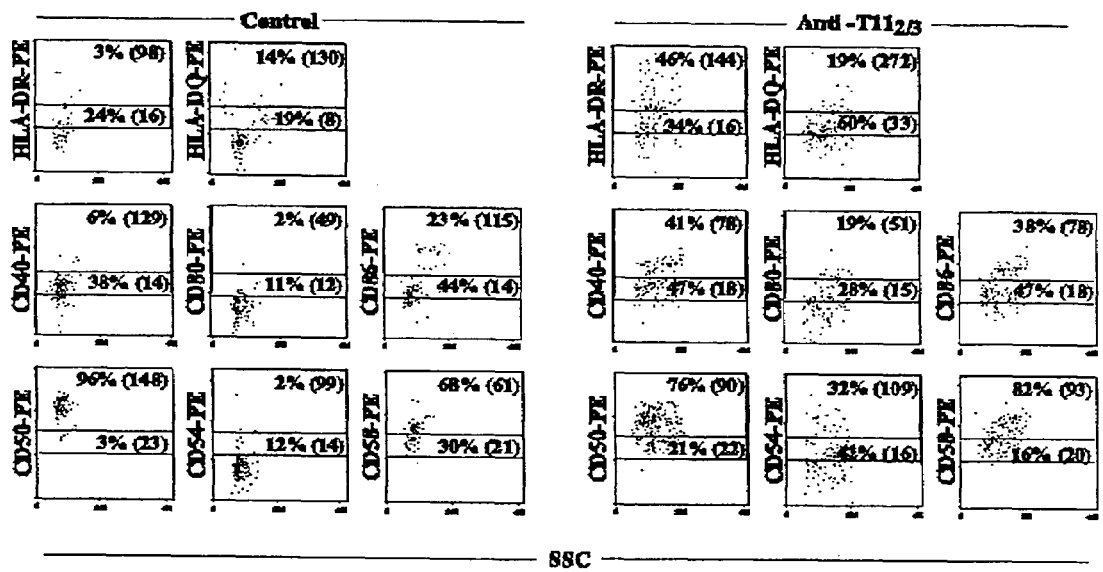
FIGS. 4A-4C is a series of graphs that illustrate the maturation and activation of mature primary dendritic cells after CD2 ligation. Primary dendritic cells were isolated and cultured for 24 hours in the presence of irrelevant antibody control, or anti-$T11_{2/3}$ monoclonal antibody pair (A&B), or anti-$T11_{1/2}$, anti-$T11_{2/3}$, or anti-$T11_{1/3}$ monoclonal antibody pairs (C). Cultures were harvested and stained as previously described in FIG. 3C. The data shown are similar to those of 3 other experiments.
Figure 4B:
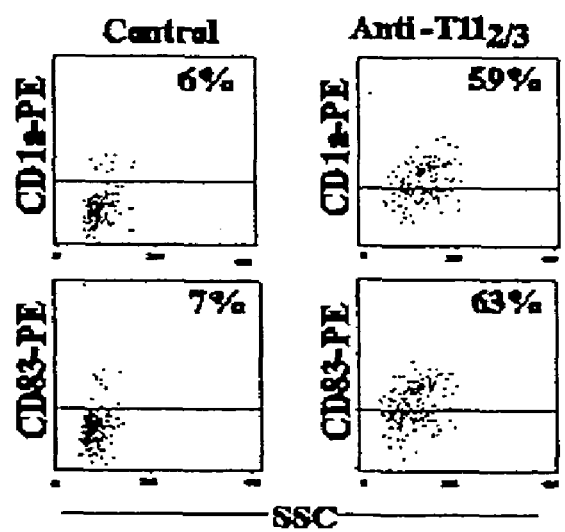
Figure 4C:
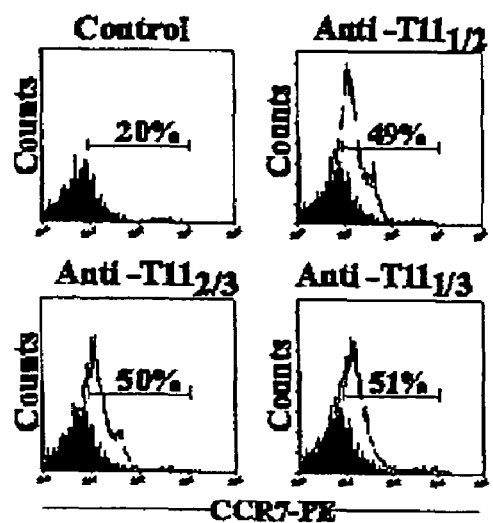

Primary dendritic cells, primary monocytes and monocyte-derived dendritic cells were assessed for their expression of Class II antigens (HLA203 DR and HLA-DQ), costimulatory antigens (CD40, CD80, and CD86), and adhesion molecules (CD50, CD54, and CD58) after 5 days of culture in 10% PHS. These cell surface antigens were expressed on no more than 12% of primary dendritic cells and 23% of primary monocytes (FIG. 3A), while they were found on greater than 96% of the monocyte-derived dendritic cells (FIG. 3B). However, when primary dendritic cells and primary monocytes were recultured in fresh medium for 24 hours, the expression of all of the above-mentioned cell surface antigens discordantly increased (FIG. 3C). Greater than 90% of the primary dendritic cells expressed CD50 and CD58 adhesion molecules, while minimal increases of other activation/maturation antigens and a decrease in cellular side scatter (a reflection of cellular activity) were noted (FIG. 3C). In contrast, a much greater percentage of the above mentioned activation/maturation antigens were expressed by primary monocytes, and no significant change in cellular side scatter was noted (FIG. 3C). Since the levels of some activation/maturation antigens on primary dendritic cells did not increase significantly after reculturing, all of the analyzed cell surface antigens on primary dendritic cells were reexamined after culture in the presence of irrelevant antibody control, or the anti-$T11_{2/3}$ mAb pair. The levels of HLA-DR and HLA-DQ expressed by primary dendritic cells cultured with the anti-$T11_{2/3}$ pair increased 2-to 3-fold compared with control cultures (FIG. 4A). The levels of costimulatory antigens CD40 and CD80 increased 2-to 3-fold respectively, while only the high expressing CD86 population increased by 65%. Greater than 96% of the control samples expressed CD50, but upon CD2 engagement the percent $CD50^{hi}$ of the primary dendritic cells decreased from 96% to 76%, and their MFI decreased from 148 to 90 (FIG. 4A). In contrast, the baseline levels of CD54 were low (14%), but increased almost 9-fold after culture with anti-CD2 pairs (FIG. 4A). Even though not as dramatic as the increase in CD54 expression, the percentage of $CD50^{hi}$ of the primary dendritic cells increased by 21% with an accompanying 53% increase in MFI. In addition, dendritic cell-specific antigens CD83 and CDla (FIG. 4B) and CCR7 (FIG. 4C) increased after CD2 engagement 9- and 2.5-fold, respectively. Collectively, these findings also correlate with the increase in cellular side scatter, and suggest that engagement of primary dendritic cells CD2 not only upregulates class II antigens, but also induces additional modifications in primary dendritic cell phenotypic properties associated with cellular activation/maturation.

Figure 5:
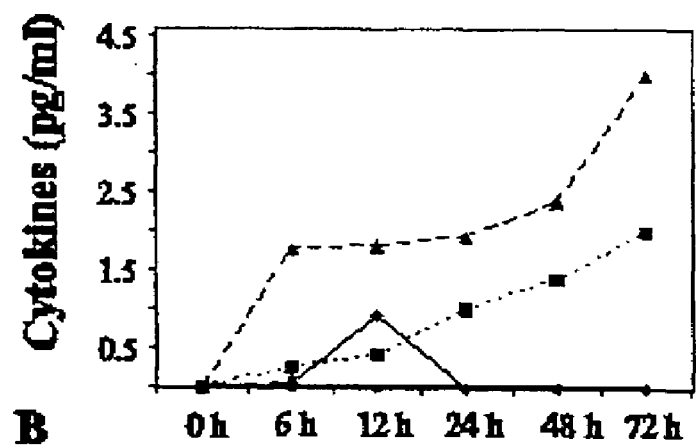
FIGS. 5A-B are line graphs illustrating that CD2 ligation induces IL-1β and IL-12 cytokine production by primary dendritic cells. Primary dendritic cells (5A) and monocyte derived dendritic cells (5B) were cultured in the presence [▲ (IL-12) and ■ (IL-1β)] or absence [♦ (IL-12) and * (IL-1β)] of anti-CD2 (T-$11_1$) monoclonal antibodies for 24 hours. The supernatants were assayed for IL-1β and IL-12 by ELISA. The result is typical of 3 similar experiments.
Figure 5:
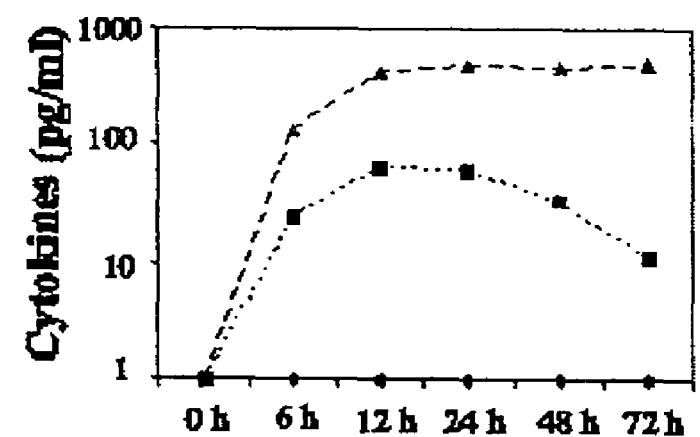

Since preliminary studies demonstrated that activation/maturation of primary dendritic cells by CD2 ligation influenced the expression of key cell surface markers that are intimately involved in T cell activation, the effects of CD2 ligation on the regulation of key innate and adaptive immune cytokines, IL-1β, and IL-12, was investigated. Both primary dendritic cells (FIG. 5A) and monocyte-derived dendritic cells (FIG. 5B) were cultured in the presence or absence of anti-$T11_1$ mAbs for 6 hours, 12 hours, 24 hours, 48 hours, and 72 hours. Control samples had no significant levels of IL-1β or IL-12, whereas anti-$T11_1$ induced high levels of release of both cytokines by primary dendritic cells and monocyte-derived dendritic cells. Furthermore, anti-$T11_1$ had a more pronounced effect on monocyte-derived dendritic cells than on primary dendritic cells, inducing the release of 75- and 100-fold higher levels of IL-1β and IL-12, respectively.

Figure 6:
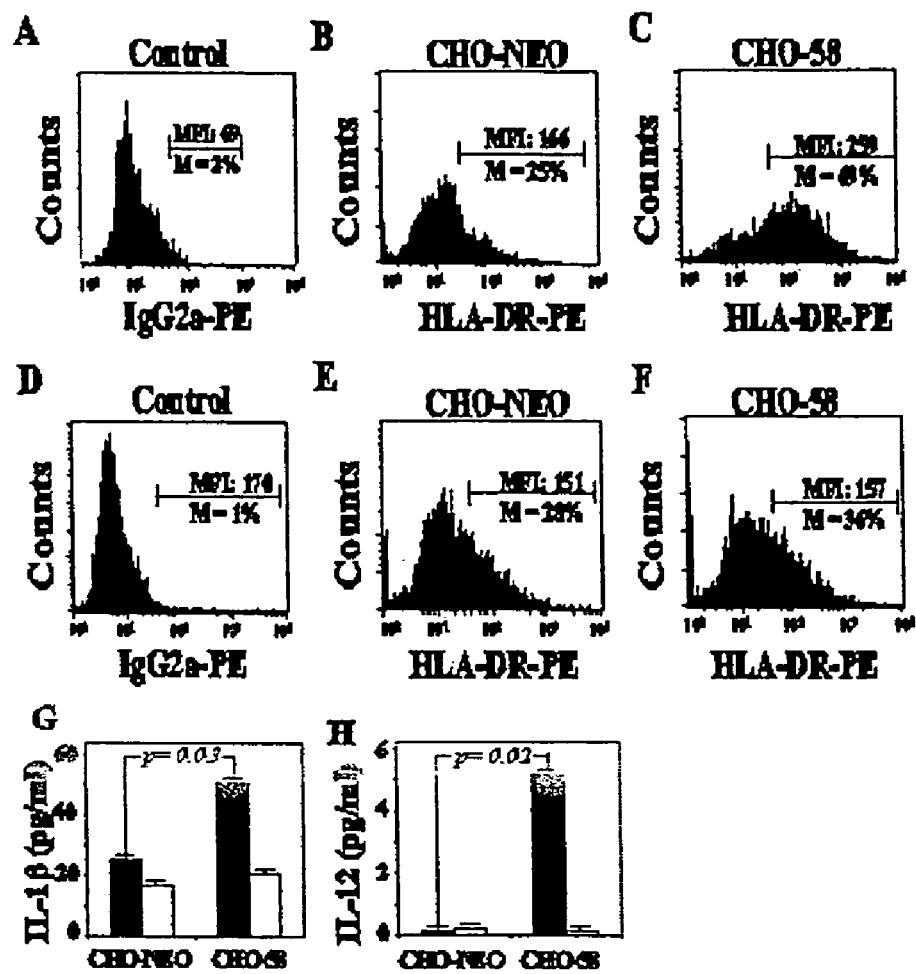
FIGS. 6A-H are graphs illustrating that CD58-transfected CHO cells induce primary dendritic cell specific increases in class II expression and IL-1β and IL-12 production. Primary dendritic cells (6A-C) and primary monocytes (6D-F) were cultured overnight in the presence of CHO-NEO (6B and 6E) or CHO-58 (6C and F). These samples were assessed by immunofluorescence analysis for the expression of HLA-DR, and the results were compared to isotype controls (6A and 6D). The supernatants from primary dendritic cells (black column) and primary monocytes (white column) cocultured in either CHO-NEO or CHO-58 were harvested, and IL-1β (6G) and IL-12 (6H) levels were measured. The results are representative of at least 3 experiments.

Primary dendritic cells were cocultured in the presence of CHO-NEO or CHO-58 cells (FIG. 6). When primary dendritic cells were cocultured with CHO-NEO (non-transfected) cells, the level of expression of HLA-DR did not increase over the level of expression with primary dendritic cells cultured alone. In contrast, when primary dendritic cells were cultured in the presence of CHO-58 cells, the level of HLA-DR increased >2.5-fold. As expected, no change in the expression of HLA-DR was noted on primary monocytes cocultured with either CHO cell population compared with primary monocytes cultured alone.

The CD58-mediated induction of cytokine production was also investigated. Analysis of supernatants from primary dendritic cells and primary monocytes cocultured with CHO-NEO and CHO-58 revealed a 2-fold increase in IL-1β (FIG. 6G) and a 26-fold increase in IL-12 (FIG. 6H) in the DC/CHO-58 cocultures compared with DC/CHO-NEO. In contrast to DC/CHO-58 cocultures, there was no significant increase in IL-1β or IL-12 levels in pMo/CHO-58 cocultures. No increase in IL-1β or IL-12 was observed when dendritic cells were cocultured with CHO58/K34A (data not shown), which possesses a single amino acid substitution in CD58 that prevents binding to CD2. These findings are consistent with previous $T11_1$-mAb pair results, and they further suggest that CD2 is a functional molecule on dendritic cells.

Figure 7:
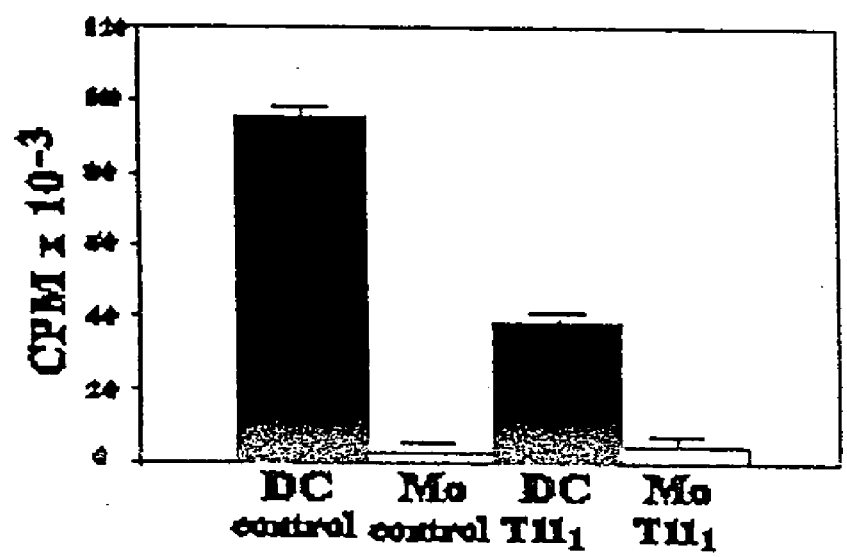
FIG. 7 is a bar graph illustrating the effects of anti-CD2 monoclonal antibodies on primary dendritic cell-induced allogenic naïve CD4 T cell activation. Primary dendritic cells and primary monocytes were cultured at 4° C. in the presence of anti-$T11_1$ or anti-$T11_2$ monoclonal antibodies. After 30 minutes, preparations were washed 3 times and resuspended in culture medium. These anti-CD2-pulsed primary dendritic cells ($10^4$) and monocytes ($10^4$) were separately cocultured with naïve CD4 T cells ($10^5$) and their ability to induce allogeneic naïve CD4 T cells to proliferate was assessed. Results are expressed as mean tritiated thymidine incorporation ±1 standard deviation, and are typical of data obtained from two similar experiments.

Primary dendritic cells were pulsed with either anti-$T11_1$ mAb, which is known to block CD2-CD58 interaction, or anti-$T11_2$ mAb, which is known not to interfere with CD2-CD58 engagement. Both cell populations were washed to remove residual mAb and cocultured with allogeneic CD4 naïve T cells for 5 days. The anti-$T11_2$-pulsed primary dendritic cells were>20 fold more efficient at naïve CD4 T cell activation than either pulsed monocyte population (FIG. 7). When compared with anti-$T11_1$ pulsed primary dendritic cells, anti-$T11_2$ pulsed primary dendritic cells were 2.5-fold more efficient at inducing T cell proliferation than either pulsed primary monocyte population (FIG. 7).

The following non-limiting examples further illustrate the present invention.

EXAMPLE 1

Isolation of Peripheral Blood Dendritic Cells and Monocytes.

This example illustrates the enrichment of monocyte and dendritic cell populations from human peripheral blood.

(a) Selection (I) of Myeloid Cells

Leukocytes from a human peripheral blood sample were placed on a discontinuous Ficoll-gradient. Centrifugation separated the peripheral blood mononuclear cells (PBMCs) from the red blood cells. The PBMC population was suspended in a magnesium-free and calcium-free 2% Hanks' balanced salt solution (HBSS) at a concentration of 108 cells per ml. 20 pl of directly conjugated mouse anti-human magnetic beads (anti-CD3, anti-CD16, anti-CD19) (MACS superparamagnetic microbeads conjugated with monoclonal anti-human CD3, CD16 or CD19 antibodies, obtained from Miltenyi Biotec, Auburn, Calif.), was added so as to deplete the T cell, NK cell and B cell lymphocytes. This suspension was incubated for 30 minutes at 4° C. and was then passed through a magnetic column (obtained from Miltenyi Biotec, Auburn, Calif.). The magnetic column subjected to the magnetic field retained the lymphocytes (T cells, NK cells and B cells) which were complexed with the antibody magnetic beads, and allowed elution of the antibodymagnetic-bead-negative PBMCs (monocytes and dendritic cells).

(b) Selection (I) of Monocytes and Dendritic Cells

The eluted cells from (a) were resuspended and washed in a centrifuge with a magnesium-free 2% Hanks' balanced salt solution (HBSS) twice for 10 minutes at 1200 rpms. To block Fc receptor non-specific binding of the Fe component, the washed cell population was resuspended in 10% human IgG-HBSS at $10^8$ cells per ml, and incubated for 30 minutes at 4° C. The addition of human IgG to the cell suspension blocks nonspecific interaction of the Fc component of the anti-CD2 monoclonal antibody. Human myeloid cells express Fc receptor to most immunoglobulins and most monoclonal antibodies used are of the IgG subtype. The human IgG will specifically bind human Fc receptor more than mouse, goat or calf immunoglobulins. The cell suspension was then washed twice to remove the unbound human IgG. Goat or rat anti-mouse magnetic beads (MACS superparamagnetic microbeadsconjugated with monoclonal anti-mouse IgG antibodies, obtained from Miltenyi Biotec, Auburn, Calif., or from Dynal Corp., Lake Success, N.Y.) were added at 100 µl per $10^9$ cells. The cell suspension was then incubated for 30 minutes at 4° C. and subsequently passed through a magnetic column (MACS) (obtained from Miltenyi Biotec). The CD2 expressing cells (dendritic cells) were retained by the magnetic beads subjected to a magnetic field as described above, while the CD2 negative cells (monocytes) passed through the magnetic field. The dendritic cells were eluted from the column by removing the column from the magnetic field and flushing with 4° C. HBSS.

The presence of dendritic cells was confirmed under light microscopic, immunofluorescent analysis and electron microscopic analysis.

(c) Selection (II) of Myeloid Cells

Peripheral blood mononuclear cells (PBMC) were isolated from anticoagulant treated blood by density centrifugation over Ficoll-Paque. The cells were resuspended in 300 µl of Buffer A: 2.5% Hanks (2.5% human serum, $Mg^{++}$ and $Ca^{++}$ free) per $1\times10^8$ cells total, and incubated for 15 minutes. A biotinylated antibody cocktail (CD3, CD19, CD16, CD56) was added to the preparation, agitated (mixed well), and incubated for 30 minutes at 4° C. After incubation, the cells were washed with buffer A and centrifuged at 300×g for 10 minutes. The supernatant was decanted and the preparation was resuspended in Buffer B: 2% Hanks (2% pooled human serum, $Mg^{++}$ and $Ca^{++}$ free). The washing was repeated and the pellet was resuspended in 900 µl of 2% Hanks per 10 cells. 100 µl streptavidin microbeads per $10^8$ total cells (final volume of 1 ml per $10^8$ total cells) was added, mixed well, and incubated for 30 minutes (15 minutes minimal) at 4° C. The cells were washed once as described above and resuspended in 1 ml of buffer per $10^8$ total cells.

A depletion column was placed in Vario MACS or Super MACs (obtained from Miltenyi Biotec, Auburn, Calif.) (see below).

| Cell number | Column type | Flowresistor | MAC separator |
|---|---|---|---|
| up to $10^7$ | BS | 22G | Vario MACs Super MACs |
| up to $2 \times 10^8$ | CS | 21G | Vario MACs Super MACs |
| up to $10^9$ | D | 20G | Super MACs |

The column was filled and rinsed with 70% EtOH. The column was then rinsed twice with buffer B, and buffer A was added and incubated for 30 minutes at 37° C. After incubation, buffer A was drained, the column was rinsed twice with buffer A, and attached to a flow resistor. The preparation (1 ml per $10^8$ cells) was added on top of the depletion column and the preparation was allowed to seep into the matrix of the column.

The column was washed with buffer and the eluted population which passed through the flow resistor was collected. This population represented the enriched myeloid population which contains both dendritic cells and monocytes.

(d) Selection (II) of Monocytes and Dendritic Cells

The non-magnetic fraction from (c) was washed and centrifuged at 300×g for 10 minutes. The supernatant was decanted, and the pellet agitated. 100 µl anti-CD2 Mab ($T11_2$) was added for a final of 200 µl, mixed well, and incubated at 4° C. for 10 minutes. The cells were washed and centrifuged at 300 g×10 minutes. The cell pellet was resuspended in 500 µl buffer B. A RS+ column combined with the RS+ column adapter was placed in a Vario MACS or Super MACS separator. (Note: If a small number of PBMC is used, approximately $10^8$ PBMC, use a RS+ column combined with the RS+ column adapter in Vario MACS or Super MACS separator. Alternatively an MS+ column in a mini MACS separator can be used.) The previous column used to deplete lymphocytes can be used to positively select the dendritic cells after the lymphocytes have been removed. The enrichment procedure in step (c) was repeated to select the magnetic population which represented dendritic cells. The enriched myeloid population was added and the dendritic cell/monocyte population was allowed to seep into the matrix. This column was washed with 3×500 µl with buffer A. After the wash was completed, the column was removed and buffer B was added to elute the magnetic fraction. The separation step was repeated twice to increase the purity of the dendritic cells. The enriched monocyte population found in the eluted population had minimal dendritic cell contamination.

EXAMPLE 2

This example illustrates a variation for enrichment of monocyte and dendritic cell populations from human peripheral blood.

Prior to the lymphocyte depletion step (the Ficoll gradient step in Example 1 used to separate granulocytes and red blood cells from blood mononuclear cells (PBMC)), PBMCs were separated into two density populations by discontinuous gradient, metrizamide (Sigma Chemical Corp., St. Louis, Mo.) or one Step (Accurate Chemical and Scientific Corp., Westbury, N.Y.) centrifugation. This step separated the lymphocyte population (T cells, B cells, NK cells) from myeloid cells in bulk. The PBMCS, at a concentration of $10^7$ cells per ml, were layered over 3 ml of 14.5% metrizamide in a 15 ml conical tube, or were layered over 12.5 ml of 14.5% metrizamide in a 50 ml conical tube. This cell suspension was spun at 1800 rpm for 10 minutes at room temperature. Two cell populations were evident by light scatter, i.e., the pelleted population which represented the high density population and the buffy layer localized at the interface which represented the low density population. The two density populations were collected and washed twice with HBSS. The majority of the high density population represented T cells, B cells, NK cells and a small population of contaminating myeloid cells, while the low density population represented dendritic cells and monocytes with a small population of contaminating lymphocytes, primarily T cells with a smaller number of B cells and NK cells.

The low density population was resuspended with HBSS. Human IgG was added and incubated for 15 minutes, and anti-CD2 ($T11^2$) was added and incubated for 30 minutes. The cells were washed, and positively selected with magnetic beads as described in Example 1.

EXAMPLE 3

This example illustrates another variation of the enrichment of monocyte and dendritic cell populations from human peripheral blood.

This method involves the direct enrichment of CD14+ myeloid cells from blood, thus eliminating the need to use a second discontinuous gradient, metrizamide, to separate lymphocytes from myeloid cells. This method is very efficient and eliminates the need to deplete contaminating lymphocytes in the myeloid population, because the red blood cells replace the magnetic beads, and lymphocyte or myeloid cell specific mAbs are attached to the red blood cells. These fractions were separated by ficoll and a Stem Cell Technologies (SCT) myeloid enrichment kit. This step separated the red blood cells and lymphocyte population (T-cells, B-cells and NK cells) together from myeloid cells (CD14+) in bulk. The SCT reagents are added to whole blood, at a concentration of $10^7$ cells per ml, combined with a myeloid enrichment cocktail and layered over 12.5 ml of the ficoll in a 50 ml conical tube. This cell suspension was spun at 1800 rpm for 30 minutes at room temperature. Two cell populations were evident by light scatter, i.e. the pelleted population, which represented the red blood cell and lymphocyte population, and the bufffy layer localized at the interface representing a relatively pure population of CD14+ mycloid cells. The CD14+ population was resuspended with HBSS. Human IgG was added and incubated for 15 minutes, and anti-CD2 ($T11_2$) was added and incubated for 30 minutes. The cells were washed, and positively selected with magnetic beads as described in Example 1.

EXAMPLE 4

This example illustrates the co-isolation of CD4+ T cells or CD8+ T cells and dendritic cells for use in clinical adoptive immunotherapy or dendritic cell T cell vaccination procedures. Adoptive immunotherapy involves the expansion of antigen/pathogen-specific T cell clones which are injected back into the patient. This example demonstrates how modification of the above-described isolation method can rapidly enrich for both T cells and dendritic cells.

The procedure involves the depletion of CD8+ T cells (or CD4+ T cells) (depending on which T cell population is desired), NK cells and B cells, by using anti-CD8 (or anti-CD4), anti-CD16, and anti-CD19 magnetic beads (obtained from Miltenyi Biotec or Dynal Corp.) or any conventional subset enrichment. The remaining cell populations were CD4+ T cells (or CD4 and CD8+ T cells), dendritic cells and monocytes. To enrich for a pure population of monocytes, anti-CD2 mABs, along with anti-CD3, anti-CD19 and anti-CD56 are used to remove T-cell, B-cell, dendritic cells and NK cells.

EXAMPLE 5

Dendritic Cell Population for Dendritic Cell-Based Vaccine in Human Patients.

This example illustrates the isolation of dendritic cells for use in vaccines. Large numbers of peripheral blood mononuclear cells (PBMC) are collected by leukapheresis. (If only small volumes are required, the procedure described in Example 1 can be used). As described in Example 2 or Example 3, the PBMC enriched population is separated into low and high density populations with a 14.5% (wt/vol) metrizamide gradient. The low density population is cultured in 10% autologous human serum for 24 hours in a humidified incubator at 37° C. supplemented with 10% $CO_2$. The high density population contains a smaller percentage of immature dendritic cells which undergoes similar treatment. Both these populations are exposed to 2 µg/ml vaccinating protein (i.e., tumor specific antigen, tetanus toxoid). After 24 hours of culturing, both populations are sequentially centrifuged through 15% and 14% (wt/vol) metriazamide gradient. This centrifugation step allows depletion of contaminating lymphocytes (i.e., removal of lymphocytes expressing CD3, CD8, CD20, and CD16 antigens). If the level of contamination by lymphoctyes is minimal by visual inspection, then depletion at this level is not necessary. The dendritic cells are immunoselected with anti-CD2 ($T11_2$) monoclonal antibodies and are subsequently activated with the $T11_3$ triggering antibody. This activated dendritic cell population is cultured again for 14-18 hours in media supplemented with protein of a 25-fold higher concentration (i.e., tumor antigen, HBsAg, tetanus toxoid). After completion of this culturing phase, the dendritic cells are resuspended in 100 ml of saline which contains 5% human serum albumin. This mixture is injected into the recipient.

EXAMPLE 6

Bone Marrow-Generated Dendritic Cells

This example illustrates the generation of dendritic cells from bone marrow. CD34+ PBMC are positively selected by immunobead selection as previously described. This CD34+ enriched population is cultured for 7-14 days in GM-CSF which induces the growth of the dendritic cell population. After a sizable number of dendritic cells are generated, they are handled in a similar fashion as the dendritic cells enriched from the peripheral blood described above.

EXAMPLE 7

Skin Dendritic Cell (Langerhan's) Enrichment

This example illustrates the generation of dendritic cells from the skin. Skin is digested overnight at 4° C. with dispase in 20% RPMI and antibiotics. Epidermis is separated and cultured in PBS supplemented with trypsin and deoxyribonuclease for 15 minutes. The cellular suspension is washed and enriched for dendritic cells in a similar fashion as the dendritic cells enriched from peripheral blood described above.

EXAMPLE 8

Engagement of CD2 on Dendritic Cells induces Maturation and Release of Cytokines.

This example illustrates that CD2 engagement on dendritic cells increases class II costimulatory (CD40, CD80 and CD86), and adhesion (CD54 and CD58) molecule expressoin on dendritic cells.

Peripheral Blood Mononuclear Cells (PBMC) were isolated from buffy coats from healthy volunteers (Transfusion Therapy, Children's Hospital, Boston, Mass.) as previously described. The PBMC were layered over a 14.5% wt/vol discontinuous Metrizamide® gradient (Sigma Chemical Co., St. Louis, Mo.) and centrifuged (Sorvall RT6000, DuPont, Wilmington, Del.) at 650×g for 10 min to separate the PBMC into low (dendritic cells and primary monocytes) and high (T, B, and NK cells) density fractions. The low-density population was depleted of contaminating leukocytes with anti-CD3, anti-CD19, and anti-CD56 immunomagnetic beads (Miltenyi Biotech, Auburn, Calif.). This negatively selected population was >98% CD14+ and negative for CD3+ T cells and CD56+ NK cells as determined by FACS analysis. These CD14+ myeloid cells served as a source of dendritic cells, primary mononuclear cells, and moncyte-derived dendritic cells. The dendritic cells were CD2-selected dendritic cells (~90% pure) and the primary mononuclear cells were obtained from the CD2-depleted eluate. CD3+ T cells were also negatively selected by depleting B cells, Mx, and NK cells from the high density population with anti-CD14, anti-CD19, anti-CD56, and anti-HLA-DR immunomagnetic beads (Miltenyi Biolec Inc.).

A previously described method was adapted to evaluate the triggering of $Ca^{++}$ flux ($[Ca^{++}]i$) by CD2 receptor crosslinking. In brief, $5\times10^6$ CD14+ Mx or CD3+ T cells were incubated with Indo-1(10 µM) (Molecular Probes, Junction City, Oreg.) in 1 ml of 1% PHS culture medium for 45 min at 37° C. Following incubation, samples were washed twice in warm RPMI, resuspended in 1% FCS, and incubated for an additional 30 min at 37° C. Changes in $[Ca^{++}]i$ in Indo-1-loaded samples were assessed with an EPICS V flow cytometer (Coulter, Hialeah, Fla.). The baseline levels were determined by measuring unstimulated Indo-1-loaded samples for 1 min, followed by sequential addition of anti-$T11_2$ [1Old-4C](dilution 1:100)] and anti-$T11_3$ [1 mono2A6 (dilution 1:100)] in 1% PHS. Goat anti-mouse IgG mAb (dilution 1:100) and the $Ca^{++}$ ionophore A23187 (5 µM)(Molecular Probes) were added to augment the response and serve as a positive control, respectively.

After 36-120 hours of culture for CD14+ Mx and 7 days of culture for monocyte-derived dendritic cells, cells were harvested and washed 3 times to remove dead cell debris and residual cytokines. After washing, the monocyte-derived dendritic cells and enriched primary dendritic cells and primary mononuclear cells were incubated at a concentration of $5\times10^5$ cells/ml in 10% PHS with mouse IgG and anti-$T11_2$ (Control), anti-$T11_1$ (SFCI3Pt2H9), and/or anti-$T11_3$. To detect cell surface Class II [HLA-DR and -DQ (Beckman Coulter, Fullerton, Calif.)], costimulatory (CD40, CD80, and CD86), adhesion (CD50, CD54, and CD58), and dendritic cell-specific (CD1a and CD83) antigens, corresponding fluorescein- or phycoerythin-conjugated mAbs were used. Supernatants were collected and stored frozen at −20° C. until tested.

To assess Class II (HLA-DP and -DM) gene expression in dendritic cells, mRNA was extracted using Dynabead Oligo (dT)25 (Dynal, Great Neck, N.Y.) from day 5-cultured primary dendritic cells ($10^5$) and primary monocytes ($10^5$) treated with or without anti-$T11_1$ or anti-$T11_3$ mAbs for an additional 24 hours. The purified mRNA was incubated with MMLV reverse transcriptase (Promega, Madison, Wis.) and random hexanucleotide primers for 1 hour at 42° C. The resulting eDNA was amplified using AmpliTaq Gold (Applied Biosystems/Roche, Branchburg, N.J.). Each 50 µl PCR reaction contained 1×PCR Gold Buffer, 25 mM $MgCl_2$, 0.25 U AmpliTaq Gold, 200 µM dNTP (Promega), and 500 ng cDNA in sterile water. Three PCR reactions were set up for each cDNA, and 20 pmol of primer pairs corresponding to HLA-DP (forward: 5'-ACGGCGTTACTGATGGTGCT-GCTC-3' (SEQ ID NO: 1); reverse: 5'-TGAATGCIGC-CTGGGTAGAAATCC-3' (SEQ ID NO:2)), HLA-DM (forward: 5'-AGATGACCTGCAAAACCACAC3' (SEQ ID NO: 3); reverse: 5'-GGCCCAAATCC'lTCCACAG-3' (SEQ ID NO:4)), Beta-actin (forward: 5'-CGACCACFITGT-CAACT-3' (SEQ ID NO: 5); reverse: 5'-AGGGGTCTA-CATGGCAAC3' (SEQ ID NO:6)) were used. Thermocycling conditions were denaturing for 1 min at 94° C., annealing for 30 seconds at 60° C., and extension for 1 min at 72° C. for 30 cycles. After completion, an additional extension for 10 min at 72° C. was performed. The PCR products were separated by electrophoresis on 2% agarose gels (FMC Bioproducts, Rockland, Me.).

Supernatants were harvested from culture samples and assayed for IL-1β and IL-12 cytokines by ELISA. UltraSensitive kits were used according to the manufacturer's instructions (Biosource Intl., Camarillo, Calif.). The lower limits of detection for the IL-12 and IL-1β kits were 0.8 pg/ml and 0.12 pg/ml, respectively.

Untransfected Chinese hamster ovary (CHO-NEO) or CHO cells transfected with and expressing CD58 (CHO-58) (Dana-Farber Cancer institute, Boston, Mass.) were constructed as described by Arulanandam et al., *Proc. Natl. Acad. Sci. U.S.A.*, 90, pages 11613-11617 (1993); Arulanandam et al., *J Exp. Med.*, 180, pages 1861-1871 (1994). Untransfected and transfected CHO were cultured in DMEM (Gibco BRL) supplemented with 10% FCS (Cellgro), F12 nutrient mixture (Gibco BRL), and 1% HEPES, 1% penicillin-streptomycin, 1% glutamine and 0.5 g/ml of G418 (Gibco BRL). Primary dendritic cells and primary monocytes ($2\times10^6$) were spread over the CHO monolayer and cultured for 24 hours in 6-well tissue culture plates.

Primary dendritic cells and primary monocytes were isolated as previously described. Enriched populations were cultured in the presence of blocking buffer, which prevents non-specific binding of mAbs, for 30 min at 4° C. and pulsed with either anti-$T11_1$ or anti-$T11_2$ mAbs for an additional 30 min at 4° C. Following this incubation, samples were washed to remove residual mAbs and resuspended in 10% PHS culture medium. Each preparation ($10^4$) of primary dendritic cells and primary monocytes was cocultured with alloreactive CD4$^+$CD45RA$^+$ naïve T cells ($10^5$) in a 96-well round bottom plate for 120 hours. Sixteen hours prior to the completion of the assay, [$^3$H]thymidine was added to the cultures to assess the level of naïve T cell proliferation.

Unpaired Student's t test was used for analysis of statistical significance. Values of p<0.05 were considered statistically significant.

EXAMPLE 9

This example illustrates the generation of fused dendritic cells from substantially pure cultures of dendritic cells. This example also illustrates the generation of fused dendritic cells from a mixture of monocytes and dendritic cells, wherein fused dendritic cells are purified from the mixture.

To produce fused dendritic cells from substantially pure cultures of dendritic cells, substantially pure cultures of dendritic cells are prepared as described above, and fused with cancer cells, e.g., adenocarcinoma cells. The dendritic cells and the cancer cells are added together, and the dendritic cell-cancer cell fusion is carried out with 50% PEG in Dulbecco's PBS without Ca$^{++}$ or MG$^{++}$ at pH 7.4. Fused cells are then plated in 24-well culture plates and cultured in the presence of HAT medium for 10-14 days. Because non-fused cells will grow firmly attached to the tissue culture flask and fused cells will be more easily removed, fused cells can be initially separated from non-fused cells by gentle pipetting. Where it is desirable to use substantially pure cultures of myeloid cells as the starting material (as opposed to substantially pure cultures of dendritic cells), fused dendritic cells are purified from other fused or non-fused myeloid cells via selection using the CD2 or CD5 antigen, as described above.

A number of embodiments of the invention have been described. Nevertheless, it will be understood that various modifications may be made without departing from the spirit and scope of the invention. Accordingly, other embodiments are within the scope of the following claims. Those skilled in the art will be able to ascertain, using no more than routine experimentation, many equivalents of the specific embodiments of the invention described herein. These and all other equivalents are intended to be encompassed by the following claims.

What is claimed is:

1. A substantially purified population of mammalian dendritic cells wherein said dendritic cells express antigen CD14 and antigen CD2.

2. The substantially purified cell population of claim 1 wherein the CD2 is ligated with ananti-CD2 antibody pair.

3. The substantially purified cell population of claim 2 wherein the anti-CD2 antibody binds to at least one of the major extracellular regions of the CD2 molecule.

4. The substantially purified cell population of claim 3 wherein the antibodies are crosslinked.

5. The substantially purified cell population of claim 1 wherein the dendritic cells are fused with cancer cells.

6. The substantially purified cell population of claim 2 wherein the anti-CD2 antibodies are selected from the group consisting of $T11_1$, $T11_2$ and $T11_3$ region antibodies.

7. A method for stimulating the production of IL-12 in vivo in a mammal comprising administering a population of substantially purified dendritic cells to the mammal, said dendritic cells expressing CD14 and CD2 antigens, wherein said dendritic cells have been activated by ligation with at least one anti-CD2 antibody.

* * * * *